(12) United States Patent
Loftsson

(10) Patent No.: US 7,115,586 B2
(45) Date of Patent: Oct. 3, 2006

(54) NON-INCLUSION CYCLODEXTRIN COMPLEXES

(75) Inventor: Thorsteinn Loftsson, Reykjavik (IS)

(73) Assignee: Decode Genetics EHF., Reykjavik (IS)

( * ) Notice: Subject to any disclaimer, the term of this patent is extended or adjusted under 35 U.S.C. 154(b) by 0 days.

(21) Appl. No.: 10/272,936

(22) Filed: Oct. 18, 2002

(65) Prior Publication Data

US 2003/0109492 A1    Jun. 12, 2003

Related U.S. Application Data

(60) Provisional application No. 60/350,008, filed on Jan. 23, 2002, provisional application No. 60/329,751, filed on Oct. 18, 2001.

(51) Int. Cl.
*A61K 31/724* (2006.01)
*A61K 31/19* (2006.01)
*C08B 30/18* (2006.01)

(52) U.S. Cl. .................... 514/58; 514/557; 514/60; 514/772.2; 514/772.3; 514/773; 514/777; 514/779; 514/781; 514/338; 514/26; 536/103; 536/120; 536/122; 536/46; 424/493; 424/440; 424/500

(58) Field of Classification Search ............ 514/58, 514/557, 60, 772.2, 772.3, 773, 777, 779, 514/781, 338, 26; 424/493, 440, 500; 536/103, 536/120, 122, 46
See application file for complete search history.

(56) References Cited

U.S. PATENT DOCUMENTS

| | | | |
|---|---|---|---|
| 5,024,998 A | 6/1991 | Bodor | |
| 5,324,718 A * | 6/1994 | Loftsson | 514/58 |
| 5,472,954 A | 12/1995 | Loftsson | |
| 5,646,131 A * | 7/1997 | Badwan et al. | 514/58 |
| 6,407,079 B1 | 6/2002 | Müller et al. | |

FOREIGN PATENT DOCUMENTS

| | | |
|---|---|---|
| EP | 0149197 B1 | 7/1985 |
| EP | 0 579 435 A1 | 1/1994 |
| JP | 62 072628 A | 4/1987 |

OTHER PUBLICATIONS

T. Loftsson et al, "Interactions Between Preservatives and 2-Hydroxypropyl-β-Cyclodextrin", *Drug Development and Industrial Pharmacy*, 18 (3), pp. 1477-1484 (1992), published by Marcel Dekker, New York, New York.

T. Loftsson et al, "Pharmaceutical Applications of Cyclodextrins. 1. Drug Solubilization", *J. Pharm. Sci.*, 85, No. 10, pp. 1017-1025 (1996), published by American Pharmaceutical Association, Easton, PA.

T. Loftsson et al, "Cyclodextrins as Pharmaceutical Excipients", *Pharmaceutical Technology Europe*, 9, pp. 26-34 (1997), published by Advanstar Communications, London, England.

(Continued)

Primary Examiner—Shaojia Anna Jiang
Assistant Examiner—Devesh Khare
(74) Attorney, Agent, or Firm—Buchanan Ingersoll & Rooney, PC

(57) ABSTRACT

The invention provides a number of methods for enhancing the aqueous solubility of an active ingredient which is insoluble or sparingly soluble in water. In one preferred embodiment, solubilization of the active ingredient is enhanced by combining it with β-cyclodextrin in an aqueous complexation medium comprising β-cyclodextrin and a negatively- or positively-charged compound which forms an inclusion or non-inclusion complex with β-cyclodextrin and its inclusion complexes.

24 Claims, 13 Drawing Sheets

OTHER PUBLICATIONS

R. Krishnamoorthy et al, "Complexation of Weak Acids and Bases with Cyclodextrins: Effects of Substrate Ionization on the Estimation and Interpretation of Association Constants", *Int'l. J. Pharm. Advances*, vol. 1, No. 3, pp. 330-343 (1996), published by Technomic Pub. Co., Lancaster, PA.

T. Loftsson et al, "Effects of 2-hydroxypropyl-β-cyclodextrin on the aqueous solubility of drugs and transdermal delivery of 17β-estradiol", *Acta Pharm. Nord.*, vol. 1, No. 4, pp. 185-194 (1989), published by Swedish Pharmaceutical Press, Stockholm, Sweden.

E. Redenti et al, "Cyclodextrin Complexes of Salts of Acidic Drugs. Thermodynamic Properties, Structural Features, and Pharmaceutical Applications", *J. Pharm. Sci.*, vol. 90, No. 8, pp. 979-985 (2001), published by Wiley-Lisa, Inc., New York, New York.

E. Redenti et al, "Drug/Cyclodextrin/Hydroxy Acid Multicomponent Systems. Properties and Pharmaceutical Applications", *J. Pharm. Sci.*, vol. 89, No. 1, pp. 1-8 (2000), published by Wiley-Lisa, Inc., New York, New York.

T. Loftsson et al, "The effect of water-soluble polymers on the aqueous solubility and complexing abilities of β-cyclodextrin", *Int. J. Pharmaceutics*, 163, pp. 115-121 (1998), published by Elsevier/North-Holland Biomedical Press, Amsterdam, The Netherlands.

B. Pose-Vilarnovo et al, *Journal of Thermal Analysis and Calorimetry*, vol. 68, pp. 657-667 (2002), published by Kluwer Academic Publishers; Dordrecht, The Netherlands.

T. Loftsson et al, "The Influence of Water-Soluble Polymers and pH on Hydroxypropyl-β-Cyclodextrin Complexation of Drugs", *Drug Devel. Ind. Pharm.*, 22(5), pp. 401-405 (1996), published by Marcel Dekker, New York, New York.

D. Attwood et al, *Surfactant Systems, Their Chemistry, Pharmacy and Biology*, pp. 361-365 (1983), published by Chapman and Hall, London, England.

*Remington's Pharmaceutical Sciences*, 18th edition, ed. Alfonso R. Gennaro, pp. 291-294 (1990), published by Mack Publishing Company, Easton, PA.

Martin et al, *Physical Pharmacy. Physical Chemical Principles in Pharmaceutical Sciences*, 3rd edition, pp. 592-638 (1983), published by Lea & Febiger, Philadelphia, PA.

Florence et al, *Physicochemical Principles of Pharmacy*, 2nd edition, pp. 281-334 (1988), published by Chapman and Hall, New York, New York.

Loftsson et al, "Cyclodextrins and drug permeability through semipermeable cellophane membranes", *International Journal of Pharmaceutics*, 232, pp. 35-43 (2002), published by Elsevier/North-Holland Biomedical Press, Amsterdam, the Netherlands.

T. Loftsson et al, "The Effects of Cyclodextrins on Transdermal Delivery of Drugs", *Eur. J. Pharm. Biopharm.*, 37 (1), pp. 30-33 (1991), published by Wissenschaftliche Verlagsgesellschat mbH, Stuttgart, Germany.

Loftsson, Thorsteinn et al., "Cyclodextrin complexation of NSAIDS: Physicochemical characteristics." European Journal of Pharmaceutical Sciences, vol. 1, No. 2, 1993, pp. 95-101, Elsevier Science B.V., Amsterdam, the Netherlands.

Loftsson, Thorsteinn et al., "The effect of polyvinylpyrrolidone and hydroxypropyl methylcellulose on HP-beta-CD complexation of hydrocortisone and its permeability through hairless mouse skin." 1994, European Journal of Pharmaceutical Sciences, vol. 2, No. 4, pp. 297-301, Elsevier Science B.V., Amsterdam, the Netherlands.

Derwent Abstracts, WPI Acc No.: 1987-132517/198719, abstract of JP 62 072628 (Apr. 3, 1987).

\* cited by examiner

A

B

NON-INCLUSION CYCLODEXTRIN COMPLEXES

CROSS-REFERENCE TO RELATED APPLICATIONS

This application claims priority under 35 U.S.C. §119(e) of U.S. Provisional Applications No. 60/329,751, filed Oct. 18, 2001 and No. 60/350,008, filed Jan. 23, 2002, both of which are incorporated by reference herein in their entireties and relied upon.

BACKGROUND OF THE INVENTION

1. Field of the Invention

This invention relates to the formation of guest/host (cyclodextrin) inclusion complex microaggregates and the non-inclusion solubilization of water-insoluble compounds within such aggregates, as well as methods for solubilizing and stabilizing the microaggregates and cyclodextrin complexes of two or more drugs where at least one drug forms an inclusion complex with cyclodextrin and at least one other drug forms a non-inclusion complex with the inclusion complex formed.

2. Background Art

Cyclodextrins are a group of structurally related saccharides that are formed by enzymatic cyclization of starch by a group of amylases termed glycosyltransferases. Cyclodextrins are cyclic oligosaccharides, consisting of ($\alpha$-1,4)-linked $\alpha$-D-glucopyranose units, with a somewhat lipophilic central cavity and a hydrophilic outer surface. Due to lack of free rotation about the bonds connecting the glucopyranose units, the cyclodextrins are not perfectly cylindrical molecules but are cone-shaped. The primary hydroxyl groups of the sugar residues are located on the narrow end of the formed cone while the wider face contains the secondary hydroxyl groups.

The most common naturally occurring cyclodextrins are $\alpha$-cyclodextrin, $\beta$-cyclodextrin and $\gamma$-cyclodextrin consisting of 6, 7 and 8 glucopyranose units, respectively. Of these three derivatives, $\beta$-cyclodextrin appears to be the most useful pharmaceutical complexing agent due to its cavity size, availability, low cost and other properties.

The natural cyclodextrins, in particular $\beta$-cyclodextrin, have limited aqueous solubility and their complex formation with lipophilic drugs often result in precipitation of solid drug-cyclodextrin complexes. Thus, the solubility of $\beta$-cyclodextrin in water is only about 18.5 mg/mL at room temperature. This low aqueous solubility is, at least partly, associated with strong intermolecular hydrogen bonding in the cyclodextrin crystal lattice. Substitution of any of the hydrogen bond-forming hydroxyl groups, even by hydrophobic moieties such as methoxy groups, will increase the aqueous solubility of $\beta$-cyclodextrin.

In addition, since these manipulations frequently produce large numbers of isomeric products, chemical modification can transform the crystalline cyclodextrins into amorphous mixtures, increasing their aqueous solubility. For example, isomeric mixtures of 2-hydroxypropyl-$\beta$-cyclodextrin are obtained by treating a base-solubilized solution of $\beta$-cyclodextrin with propylene oxide. The aqueous solubility of 2-hydroxypropyl-$\beta$-cyclodextrin is over 60 g/100 mL. These cyclodextrin systems resemble, therefore, other pharmaceutical starches, such as hydroxypropyl cellulose, in terms of the complexity of their composition. Both the molar substitution, i.e., the average number of propylene oxide molecules that have reacted with one glucopyranose unit, and the location of the hydroxypropyl groups on the $\beta$-cyclodextrin molecule will affect the complexation properties of the 2-hydroxypropyl-$\beta$-cyclodextrin mixture. Other cyclodextrin derivatives of current pharmaceutical interest include the analogous hydroxypropyl derivatives of $\alpha$- and $\gamma$-cyclodextrin, sulfoalkyl ether cyclodextrins such as sulfobutylether $\beta$-cyclodextrin, alkylated cyclodextrins such as the randomly methylated $\beta$-cyclodextrin, and various branched cyclodextrins such as glucosyl- and maltosyl-$\beta$-cyclodextrin.

In aqueous solutions cyclodextrins form complexes with many drugs, as well as other molecules, which possess somewhat hydrophobic moieties capable of entering the somewhat lipophilic central cavity, through a process in which the water molecules located in the cavity are replaced by this hydrophobic moiety. In some cases, small lipophilic water-insoluble drugs (or other small lipophilic compounds) are completely encapsulated by the cyclodextrin molecule, but in most cases the drug molecules are too large and thus will only be partly encapsulated by the cyclodextrin molecule. The drug molecule is called the guest molecule and the cyclodextrin molecule the host molecule. The cyclodextrin cavity is relatively hydrophobic due to the presence of the skeletal carbons and ethereal oxygens that comprise the cavity. Since the water molecules located inside the cavity cannot satisfy their hydrogen-bonding potential, they are of higher enthalpy than bulk water molecules located in the solution. The main driving force for complex formation, at least in the case of $\beta$-cyclodextrin and its derivatives, appears to be the release of these enthalphy-rich water molecules from the cavity, which lowers the energy of the system. Once included in the cyclodextrin cavity, the guest molecules may be dissociated through complex dilution, by replacement of the included guest by some other suitable molecule (such as dietary lipids or bile salts in the GI tract) or, if the complex is located in close proximity to a lipophilic biological membrane (such as the mucosal membrane of the GI tract), the guest may be transferred to the matrix for which it has the highest affinity. Importantly, since no covalent bonds are formed or broken during the drug-cyclodextrin complex formation, the complexes are in dynamic equilibrium with free drug and cyclodextrin molecules.

One of the main obstacles of pharmaceutical applications of cyclodextrins is their complexation efficiency. For a variety of reasons, including toxicological considerations, formulation bulk and production cost, it is important to use as little cyclodextrin as possible in pharmaceutical preparations. Unfortunately, the complexation efficiency of cyclodextrins is frequently rather low, in which case large amounts of cyclodextrin are needed to complex relatively small amounts of drug. Common pharmaceutical additives, such as surfactants, buffer salts, preservatives and organic solvents, can reduce the efficiency even further (T. LOFTSSON, O. STEFANSDOTTIR, H. FRIDRIKSDOTTIR and O. GUDMUNDSSON: Interactions between preservatives and 2-hydroxypropyl-$\beta$-cyclodextrin. *Drug Devel. INd. Pharm.;* 18, 1477–1484, 1992; T. LOFTSSON and M. E. BREWSTER: Pharmaceutical applications of cyclodextrins. 1. Drug solubiization and stabilization. *J. Pharm. Sci.;* 85, 1017–1025, 1996). Normally solid drug-cyclodextrin complexes contain less that 5 to 10% of the drug. It is therefore important to develop methods that can be applied to enhance the complexation efficiency of cyclodextrins. In the past, the following methods have been applied in an effort to enhance the complexation efficacy of cyclodextrins, all of which assume that cyclodextrins interact with drug molecules on molecular bases through formation of inclusion complexes without further association or aggregation (T. LOFTSSON and M. E. BREWSTER: Cyclodextrins as Pharmaceutical Excipients. *Pharmaceutical Technology Europe;* 9, 26–34, 1997):

Unionized drugs usually form more stable cyclodextrin complexes than their ionic counterparts. However, it is sometimes possible to enhance cyclodextrin solubilization of ionizable drugs by appropriate pH adjustments (R. KRISHNAMOORTHY AND A. K. MITRA: Complexation of weak acids and bases with cyclodextrins: Effects of substrate ionization on the estimation and interpretation of association constants, *Int. .J. Pharm. Advances,* 1, 330–343, 1996; T. LOFTSSON AND N. BODOR: Effects of 2-hydroxypropyl-β-cyclodextrin on the aqueous solubility of drugs and transdermal delivery of 17β-estradiol, *Acta Pharm.Nord.,* 1, 185–194; 1989; E. REDENTI, L. SZENTE AND J. SZEJTLI: Cyclodextrin Complexes of Salts of Acidic Drugs. Thermodynamic Properties, Structural Features, and Pharmaceutical Applications. *J. Pharm. Sci.,* 90, 979–986, 2001). In this case the solubilization is increased due to increased intrinsic solubility of the drug obtained through ionization of the drug molecule. Furthermore, formation of water-soluble salts between a basic drug and an organic acid (such as lactic acid), or an acidic drug and organic base (such as tromethamine) can enhance the complexation due to lowering of the melting point of the solid drug which in turn increases the intrinsic solubility of the drug. See also BADWAN ET AL. U.S. Pat. No. 5,646,131.

Addition of certain low molecular weight acids, such as acetic, citric, malic, or tartaric acid, to aqueous complexation media can enhance cyclodextrin solubilization of basic drugs as well as increase complexation efficiency (E. REDENTI, L. SZENTE AND J. SZEJTLI: Drug/Cyclodextrin/Hydroxy Acid Multicomponent Systems. Properties and Pharmaceutical Applications. *J. Pharm. Sci.,* 89, 1–8, 2000). Enhanced complexation is obtained through formation of free (i.e., un-aggregated) drug-hydroxy acid-cyclodextrin ternary complexes with basic drugs. In all cases the drug has to be a proton acceptor capable of forming an ion pair or salt with the acid. BADWAN ET AL., in U.S. Pat. No. 5,646,131, describe a method for enhancing the solubilization of a drug which is insoluble or sparingly soluble in water by combining the drug in water with cyclodextrin and a saturated or unsaturated $C_2$–$C_6$ carboxylic acid having 1 to 3 COOH groups and 0 to 4 OH groups, provided that when the acid has only one COOH group, it must bear at least one OH group, or a salt of the acid, the weight ratio of cyclodextrin to carboxylic acid being from 1:50 to 5:1. Preferred are citric acid, glutaric acid, lactic acid, tartaric acid and their salts. Basic drugs are of particular interest.

Water-soluble Polymers

It has been shown that various pharmaceutical polymers, such as water-soluble cellulose derivatives and other rheological agents, can form complexes with cyclodextrins and that such complexes possess physicochemical properties distinct from those of individual cyclodextrin molecules (THORSTEINN LOFTSSON: Cyclodextrin/drug complexation, U.S. Pat. No.: 5,324,718 (Filed: Jul. 14, 1992; Issued: Jun. 28, 1994); THORSTEINN LOFTSSON: Cyclodextrin Complexation, U.S. Pat. No. 5,472,954 (Filed: May 11, 1994; Issued: Dec. 5, 1995)). In aqueous solutions, water-soluble polymers increase the solubilizing effect of cyclodextrins on various hydrophobic drugs by increasing the apparent stability constants of the drug-cyclodextrin complexes. See also T. LOFTSSON AND H. FRIDRIKSDOTTIR: The effect of water-soluble polymers on the aqueous solubility and complexing abilities of β-cyclodextrin. *Int. J. Pharmaceutics,* 163, 115–121, 1998; and B. POSE-VILARNOVO ET AL., *Journal of Thermal Analysis and Calorimetry,* Vol. 68, 657–667, 2002.

Combination Methods

Finlly, it is often possible to enhance cyclodextrin complexation even further by using several different methods simotaneously to enhance the cyclodexrin complexation (T. LOFTSSON, T.K. GUDMUNDSDOTTIR AND H. FRIDRIKSDOTTIR: The Influance of Water-Soluable Polymers and pH on Hydroxypropyl-β-Cyclodextrin of Drugs. *Drug Devel. Ind. Pharm.,* 22, 401–405, 1996).

SUMMARY AND OBJECTS OF THE INVENTION

The present invention involves formation of guest/host inclusion complex microaggregates and their industrial applications. These aggregates are invisible to the human eye and cannot be detected by a conventional light microscope and, thus, their diameter is less than the wavelength of visible light (less than about 600 nm). Because they in most cases do not produce light scattering, their diameter is most probably less than one quarter of the wavelength of visible light, or less than about 140 nm. Such microaggregates will appear transparent or translucent due to diminished light scattering. The diameter of β-cyclodextrin is approximately 1.5 nm.

More specifically, the present invention involves non-inclusion solubilization of water-insoluble compounds within such aggregates. Such systems consist of cyclodextrin (host), lipophilic or hydrophilic compound which is able to form an inclusion complex with cyclodextrin (guest) and compound which does not readily form a complex with cyclodextrin (accompanying guest). The guest can be a water-soluble compound but it must be able to form an inclusion complex with cyclodextrin. The accompanying guest is predominately included within the microaggregate without forming an inclusion complex with the cyclodextrin, a structure that resembles solubilization of the accompanying guest in a microemulsion in which the guest/host inclusion complexes form the surfactant.

Furthermore, this invention involves stabilization of such microaggregate systems by including polymers. Polymers are well-known to stabilize micelles (as well as other microparticular systems), i.e., regular emulsions which sometimes are called macroemulsions, and to enhance their ability to solubilize water-insoluble compounds (D. ATTWOOD AND A. T. FLORENCE: *Surfactant Systems, their Chemistry, Pharmacy and Biology,*Chapman and Hall, London, 1983, pp. 361–365).

Another aspect of this invention is inclusion of a component which solubilizes and stabilizes the microaggregate. These components can have comparable effects to those of cosurfactants in microemulsions, i.e., to enhance the stability of the microaggregates and prevent further aggregation and precipitation, and/or enhance their solubilizing effect.

In one aspect of the invention (A), there is thus provided a method for enhancing the aqueous solubility of an active ingredient which is insoluble or sparingly soluble in water, said active ingredient being a drug, cosmetic additive, food additive or agrochemical, said method comprising combining said active ingredient with β-cyclodextrin in an aqueous complexation medium, said medium comprising from about 0.1% to about 80% (weight/volume) of β-cyclodextrin and from about 0. 1% to about 5% (weight/volume) of a negatively- or positively-charged compound which forms an inclusion or non-inclusion complex with β-cyclodextrin and its inclusion complexes, said charged compound being acceptable for use in a pharmaceutical, cosmetic, food or agricultural composition.

In another aspect of the invention (B), there is provided a method for enhancing the aqueous solubility of an active ingredient which is insoluble or sparingly soluble in water, said active ingredient being a drug, cosmetic additive, food additive or agrochemical, said method comprising combining said active ingredient with β-cyclodextrin in an aqueous complexation medium, said medium comprising from about 0.1% to about 80% (weight/volume) of β-cyclodextrin; from about 0.1% to about 10% (weight/volume) of a pharmaceutically inactive water-soluble polymer acceptable for use in a pharmaceutical, cosmetic, food or agricultural composition; and from about 0.1% to about 5% (weight/volume) of a negatively- or positively-charged compound which forms an inclusion or non-inclusion complex with β-cyclodextrin and its inclusion complexes, said charged compound being acceptable for use in a pharmaceutical, cosmetic, food or agricultural composition.

In still another aspect of the invention (C), there is provided a method for enhancing the aqueous solubility of an active ingredient which is insoluble or sparingly soluble in water and which does not readily form an inclusion complex with cyclodextrin, said active ingredient being a drug, cosmetic additive, food additive or agrochemical, said method comprising adding said active ingredient to an aqueous complexation medium which comprises from about 0.1% to about 70% (weight/volume) of said cyclodextrin, said complexation medium being saturated, prior to addition of said active ingredient, with a compound which forms an inclusion complex with said cyclodextrin and which is acceptable for use in a pharmaceutical, cosmetic, food or agricultural composition.

In yet another aspect of the invention (D), there is provided a method for enhancing the aqueous solubility of an active ingredient which is insoluble or sparingly soluble in water and which does not readily form an inclusion complex with cyclodextrin, said active ingredient being a drug, cosmetic additive, food additive or agrochemical, said method comprising adding said active ingredient to an aqueous complexation medium which comprises from about 0.1% to about 70% (weight/volume) of said cyclodextrin and from about 0.01% to about 10% (weight/volume) of a pharmacologically inactive water-soluble polymer acceptable for use in a pharmaceutical, cosmetic, food or agricultural composition, said complexation medium being saturated, prior to addition of said active ingredient, with a compound which forms an inclusion complex with said cyclodextrin and which is acceptable for use in a pharmaceutical, cosmetic, food or agricultural composition.

BRIEF DESCRIPTION OF THE DRAWINGS

These and other objects and advantages of the present invention will be apparent from the following detailed description and accompanying drawings.

DETAILED DESCRIPTION OF THE INVENTION AND PREFERRED EMBODIMENTS

Figure 1:
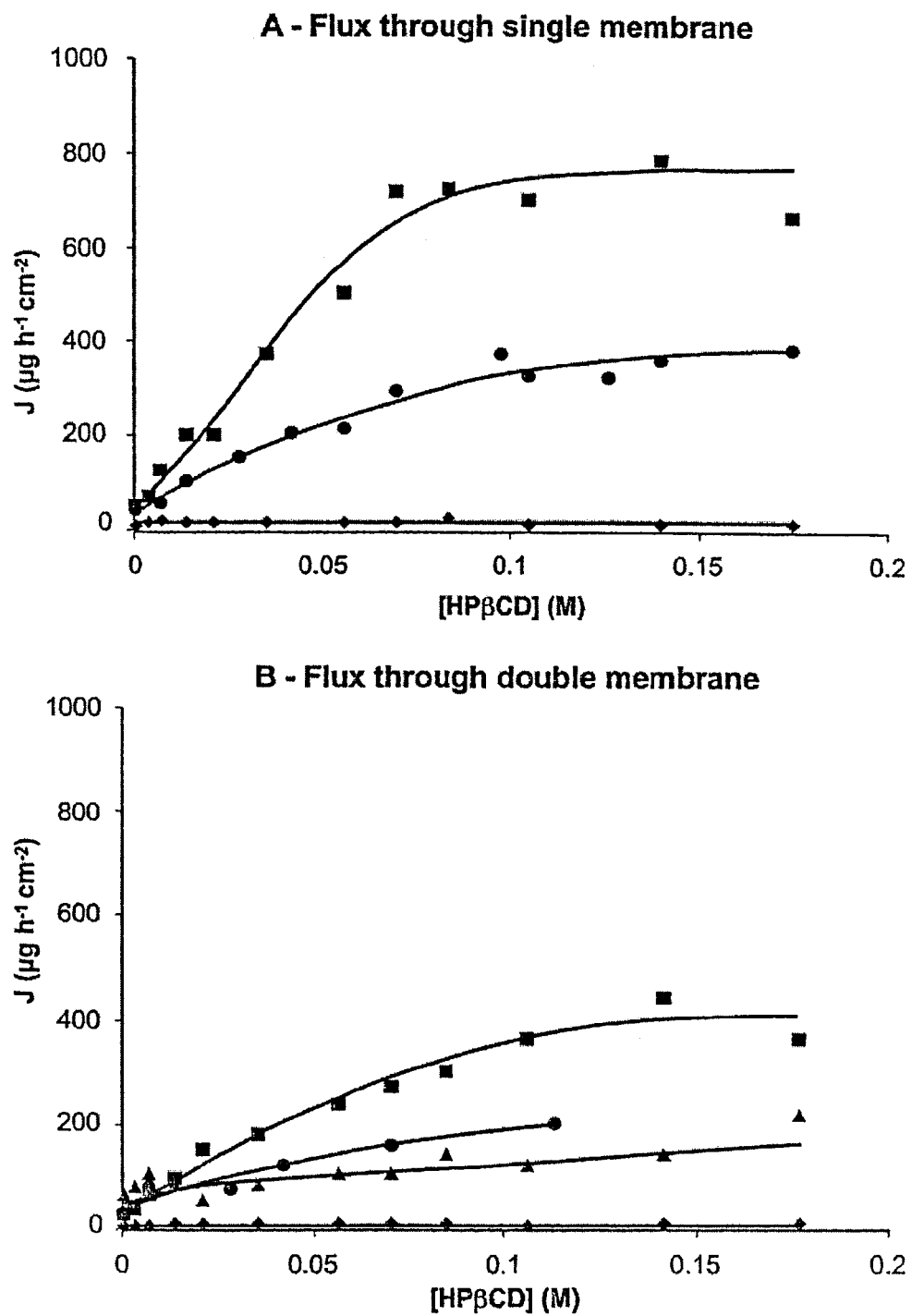
FIG. 1 is a pair of graphs illustrating the effect of the concentration of hydroxypropyl-β-cyclodextrin (HPβCD) on the flux (J) of hydrocortisone from aqueous solution, saturated with hydrocortisone, through a single layer (A) and a double layer (B) of semi-permeable cellophane membrane, where the membrane material was MWCD 500 (♦), MWCO 3,500 (▲), MWCO 6,000–8,000 (●) and MWCO 12,000–14,000 (■), MWCO being the molecular weight cutoff for the semi-permeable cellophane membranes.

Cyclodextrins for use in the present invention in aspects (C) and (D) summarized above include the natural cyclodextrins and their derivatives, including the alkylated and hydroxyalkylated derivatives and the branched cyclodextrins. Cyclodextrins and their derivatives which have been previously described as useful for complexation with drugs are of particular interest herein. In addition to α-, β-, and γ-cyclodextrins, the ether and mixed ether derivatives and those derivatives bearing sugar residues are of special interest. Especially useful herein are the hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α-, β-, and γ-cyclodextrin; the maltosyl, glucosyl and maltotriosyl derivatives of α-, β-, and γ-cyclodextrin, which may contain one or more sugar residues, e.g., glucosyl or diglucosyl, maltosyl or dimaltosyl, as well as various mixtures thereof, e.g., a mixture of maltosyl and dimaltosyl derivatives; and the variously substituted sulfoalkyl ethers of α-, β-, and γ-cyclodextrins, particularly when the alkyl group is of moderate length such as $C_4$–$C_8$. Specific cyclodextrin derivatives for use herein include hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-γ-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin and dimaltosyl-β-cyclodextrin, and mixtures thereof such as maltosyl-β-cyclodextrin/dimaltosyl-β-cyclodextrin, as well as methyl-β-cyclodextrin, and the sulfobutyl ether and sulfoheptyl ether derivatives of β-cyclodextrin (developed by CyDex, Kansas City, Kans.). Procedures for preparing the various cyclodextrin derivatives named above are well-known, for example, from Bodor U.S. Pat. No. 5,024,998 dated Jun. 18, 1991, and references cited therein. Particularly preferred cyclodextrins for use in the present invention are γ-cyclodextrin, α-cyclodextrin, β-cyclodextrin, and the hydroxypropyl, hydroxyethyl, dihydroxypropyl, glucosyl, maltosyl, methylated and sulfobutyl ether derivatives of α-, β-, and γ-cyclodextrin, and their mixtures, especially those having a molar degree of substitution of from about 0.05 to about 10. The expression "molar degree of substitution" is used in the same sense as employed in Brauns and Müller European Patent No. 0149197 B1.

In the case of aspects (A) and (B) of the invention as summarized hereinabove, the cyclodextrin is β-cyclodextrin, i.e., the natural, non-derivatized cyclodextrin. The reasons for particular interest in improving complexation with this natural cyclodextrin, which can be achieved in accord with the present invention, are discussed below.

FDA has introduced a Biopharmaceutics Classification System (BCS) for oral drug products. In this system, drugs are classified into four groups based on the ability of a given drug substance to permeate biological membranes and its aqueous solubility. The groups/classes are as follows:

Class I: highly soluble; highly permeable
Class II: poorly soluble; highly permeable
Class III: highly soluble; poorly permeable
Class IV: poorly soluble; poorly permeable In the BCS, a given drug substance is considered "highly soluble" when the highest dose strength is soluble in less than 250 mL of water over a pH range of 1 to 7.5 and "highly permeable" when the extent of absorption in humans is determined to be ≧90% of an administered dose (in solution), based on mass-balance or related to an intravenous reference dose. Thus, for rapidly dissolving solid oral dosage forms (like conventional tablets), the dose-to-solubility ratio (D:S) of the drug must be less than 250 mL over a pH range of 1 to 7.5. For other types of solid dosage forms (such as sublingual or buccal tablets, and rectal and vaginal tablets), the D:S ratio must be less than 5 to 10 mL.

Class I consists of water-soluble drugs that are well-absorbed from the gastrointestinal tract and, in general, have the preferred physicochemical properties. For immediate release dosage forms, the absorption rate will be controlled by the gastric emptying rate. However, to secure constant high bioavailability, the dissolution rate must be relatively fast, or over 85% dissolution in 15 minutes.

Class II consists of water-insoluble drugs which, when dissolved, are well-absorbed from the gastrointestinal tract. The dissolution rate in vivo is usually the rate-limiting step in drug absorption.

Class III consists of water-soluble drugs that do not readily permeate biomembranes. For these drugs, the rate-limiting factor in drug absorption is their permeability.

Class IV consists of water-insoluble drugs which when solubilized do not readily penetrate biomembranes. These drugs are usually very difficult to formulate for effective oral delivery.

Through complexation with water-soluble cyclodextrins it is possible to move Class II drugs, and sometimes even Class IV drugs, into Class I by increasing their apparent solubility in water. The natural cyclodextrins and their complexes have, however, limited aqueous solubility. For example, the solubility of β-cyclodextrin in water is only about 18.5 mg/mL at room temperature and the maximum amount of hydrocortisone which can be dissolved in saturated β-cyclodextrin solution (water saturated with β-cyclodextrin) is 2.2 mg/mL (See Tables 3 and 4 in Experiments C and D to follow). Various water-soluble cyclodextrin derivatives have been synthesized. These derivatives and their complexes are much more water-soluble than the parent β-cyclodextrin. Cyclodextrin derivatives of current pharmaceutical interest include 2-hydroxypropyl-β-cyclodextrin, 2-hydroxypropyl-γ-cyclodextrin, sulfobutyl ether β-cyclodextrin, randomly methylated β-cyclodextrin, and some branched cyclodextrins such as maltosyl-β-cyclodextrin. See the following Table.

TABLE

Natural cyclodextrins and some of their derivatives that are currently used in pharmaceutical products.

| Cyclodextrin | Substitution[a] | Mw[b] | Solubility in water (mg/mL)[c] |
|---|---|---|---|
| α-Cyclodextrin | — | 972 | 145 |
| β-Cyclodextrin | — | 1135 | 185 |
| 2-Hydroxypropyl-β-cyclodextrin | 0.65 | 1400 | >600 |
| Randomly methylated β-cyclodextrin | 1.8 | 1312 | >500 |
| β-cyclodextrin sulfobutyl ether sodium salt | 0.9 | 2163 | >500 |
| γ-Cyclodextrin | — | 1297 | 232 |
| 2-Hydroxypropyl-γ-cyclodextrin | 0.6 | 1576 | >500 |

[a]Average number of substituents per glucopyranose repeat unit.
[b]MW given by the supplier, or the calculated value based on the average degree of substitution, for the water-free substance.
[c]Solubility in pure water at approximately 25° C.

Including cyclodextrins in pharmaceutical formulations will increase the formulation bulk of solid dosage forms. Even under the best conditions, cyclodextrin complexation will on the average result in about a 10-fold increase in the formulation bulk. This limits the use of cyclodextrins in solid oral dosage forms to relatively potent drugs that possess good complexing properties. Cyclodextrin derivatives have greater molecular weight (MW) than their parent cyclodextrins and thus result in greater increase in the formulation bulk, i.e., in the case of natural cyclodextrins, the drug occupies a greater fraction of the complex powder. Based on the molecular weights given in the above Table, it can be seen that if the cyclodextrin derivatives can be replaced by the natural cyclodextrin, the formulation bulk will be decreased by as much as 50%. However, this can only be done if the D:S ratio is below 250 mL for conventional oral formulations (e.g., tablets and capsules) and, for example, below 5 mL for sublingual tablets. By the present invention, the aqueous solubility of β-cyclodextrin and its complexes can be enhanced, lowering the D:S ratio to an acceptable level, in other words, to a level which is sufficient to move a given water-insoluble drug from Class II to Class I.

Suitable polymers for use herein in aspects (B) and (D) summarized above are those which are soluble in water, are acceptable for use in pharmaceuticals and are pharmacologically inactive. Such polymers are well-known excipients commonly used in the field of pharmaceutical formulations. [See, for example, *Remington's Pharmaceutical Sciences*, 18th edition, Alfonso R. Gennaro (editor), Mack Publishing Company, Easton, Pa., 1990, pp. 291–294; ALFRED MARTIN, JAMES SWARBRICK AND ARTHUR COMMARAM, *Physical Pharmacy. Physical Chemical Principles in Pharmaceutical Sciences*, 3rd edition, Lea & Febinger, Philadelphia, Pa., 1983, pp. 592–638; A. T. FLORENCE AND D. ATTWOOD, *Physicochemical Principles of Pharmacy*, 2nd edition, Chapman and Hall, New York, N.Y. 1988,PP. 281–334.] Suitable polymers include water-soluble natural polymers, water-soluble semisynthetic polymers (such as the water-soluble derivatives of cellulose) and water-soluble synthetic polymers. The natural polymers include polysaccharides such as inulin, pectins, algin derivatives (e.g., sodium alginate) and agar, and polypeptides such as casein and gelatin. The semisynthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g., carbomer). Other natural, semi-synthetic and synthetic polymers not named here which meet the criteria of water solubility, pharmaceutical acceptability and pharmacological inactivity are likewise considered to be within the ambit of the present invention. Particularly preferred polymers for use herein are sodium carboxymethylcellulose, hydroxypropyl methylcellulose and polyvinylpyrrolidone.

Water-soluble polymers for use with drugs herein, as pointed out above, need to be pharmaceutically acceptable and pharmacologically inactive. Generally speaking, such water-soluble polymers will also be acceptable for use with food additives, cosmetic additives and agrochemicals (agricultural chemicals), since the most stringent requirements are usually placed on pharmaceuticals, particularly for parenteral use. Conversely, however, a polymer which is not pharmaceutically acceptable could, for example, nevertheless be agriculturally acceptable, particularly for non-crop applications; such a polymer is intended for use herein in compositions with those non-drug materials, e.g., agrochemicals, which do not require pharmaceutical acceptability. Similarly, the water-soluble polymers for use with food and cosmetic additives need only be acceptable for use in foods and cosmetics.

As insoluble or sparingly soluble food additives which are contemplated herein for use, there can be mentioned, by way of example, flavoring agents, preservatives, antioxidants, sweetening agents, vitamins and coloring agents. Illustrative of such additives are flavors such as vanillin, aromatic flavoring oils such as lemon oil, cinnamon oil, oil of anise, oil of bitter almond or benzaldehyde, oil of clove, oil of orange, oil of peppermint, garlic oil, onion oil and menthol; sweeteners such as aspartame and saccharin; colors such as methyl yellow as well as natural colors; preservatives such as methylparaben, propylparaben, chlorbutol, benzoic acid and salicylic acid; and antioxidants such as butylated hydroxyanisol. Some food additives may also be classified as drugs, e.g., the vitamins, discussed in more detail hereinbelow.

In the case of cosmetic additives contemplated for use in this invention, many of the same classes of ingredients (including some of the same specific ingredients) noted above as food additives are intended; in some cases, cosmetic additives may also be classified as drugs as discussed more fully below, for example, the vitamins, including the retinoids. Illustrative classes of cosmetic additives include preservatives, antioxidants, aromatic oils (fragrances), coloring agents and vitamins (also noted as drugs herein). Specific additives of interest for cosmetics include fragrant aromatic oils such as lavender oil, pine oil, oil of geranium, oil of rose, oil of sweet bay, oil of lemon, oil of lemon grass, preservatives such as camphor and vitamins such as vitamin $D_2$ (cholecalciferol), vitamin $D_3$, and vitamin E, as well as vitamin A and the other retinoids such as retinoic acid.

With regard to agrochemicals, those contemplated for use in this invention include pesticides (including, for example, insecticides and nematocides), fungicides, herbicides and plant growth regulators. Illustrative of such agrochemicals are pesticides such as pentachlorophenol, mevinphos, piperonyl butoxide, hydroprene, methoprene and kinoprene; fungicides such as 4-chloro-3-methylbenzothiazolone and pyrrolnitrin; and herbicides such as pentachlorophenol and 2,6-dichlorobenzonitrile. Yet other agrochemicals contemplated for use in the instant methods and compositions include herbicides such as atrazine, barban, bromoxynil, butachlor, carbetamide, chlorpropham, chlortoluron, 2,4-D, 2,4-DB, diallate, dicamba, dichlorprop, diuron, EPTC, ethofumesate, fluometuron, ioxynil, isoproturon, linuron, MCPA, mecoprop, metamitron, methabenzthiazuron, metribuzin, oxadiazon, pebulate, phenmedipham, prometryn, propachlor, propanil, propham, simazine, thiobencarb, isoxaflutole, triallate and trifluralin; fungicides such as 2,6-dimethyl-4-tridecylmorpholine, methyl N-(1-butylcarbarmoylbenzimidazol-2-yl)carbamate, 1,2-bis(3-methoxycarbonyl-2-thioureido)benzene, isopropyl 1-carbamoyl-3-(3,5-dichlorophenyl)hydantoin and 1-(4-chlorophenoxy)-3,3-dimethyl-1-(1,2,4-triazol-1-yl)butan-2-one; acaricides such as dicofol and antiparasitic antibiotics, such as ivermectin, avermectins and milbemycins, which are also insecticidal; and insecticides such as chlorpyrifos, dementon-S-methyl, disulfoton, ethoprofos (or ethoprop), fenitrothion, malathion, parathion, phosalone, cyfuthrin, cypermethrin, deltamethrin, fenpropathrin, fenvalerate, permethrin, bendiocarb, endosulfan, lindane, fipronil, and synthetic pyrethroids, for example, permetrin and cypermethrin.

It is well-known that a number of food and cosmetic additives, particularly flavors, fragrances and colors, as well as agrochemicals (pesticides, herbicides, insecticides and fungicides) can be complexed with cyclodextrin, while others cannot be.

Among the insoluble or sparingly soluble drugs which are contemplated for use in the methods of the present invention, there can be mentioned antineoplastics (anticancer/antitumor agents), sedatives, antiinflammatory steroids (glucocorticoids), tranquilizers, anticonvulsants, antivirals, antihistaminics, vitamins/nutritional factors, emetics, anticoagulants, cardiotonics (including cardiac glycosides), diuretics, non-steroidal analgesic and/or anti-inflammatory agents (NSAID's), androgens, estrogens, anabolic agents, vasodilators, antidepressants, antipsychotics, hypnotics, antifungals, progestins, antiprotozoals, anthelmintics, anesthetics, vasoconstrictors, hypoglycemics, antibacterials/antibiotics, and anti-infectives, platelet inhibitors, muscle relaxants, antiemetics, radiodiagnostics, antispasmodics, antiarrythmics, carbonic anhydrase inhibitors, gastrointestinal agents (including $H_2$-antagonists and other anti-ulcer agents), antihypertensives especially including those useful as anti-glaucoma agents, serotonin antagonists, narcotic antagonists, narcotic agonists, mixed narcotic agonists-antagonists, pharmacologically active proteins such as peptide hormones, enzymes, antibodies and other biologically produced substances, anti-Parkinsonism/dopamineric agents and drugs for treating Alzheimer's disease.

It is now well-known that insoluble or sparingly soluble drugs which complex with cyclodextrin have the required shape and size to fit at least partially into the cavity of the hydrated cyclodextrin molecule; see, for example, Brauns and Müller European Patent No. 0149197 B1. Drugs whose water solubility can be improved by complexation with cyclodextrins exhibit significantly increased complexation and water solubility when treated in accord with the present invention.

Specific drugs contemplated for use in the present invention include antineoplastics such as chlorambucil, lomustine, melphalan, methotrexate, hexamethylmelamine, teniposide, etoposide, semustine (methyl CCNU), fazarabine (Ara-AC), mercaptopurine, tubulazole, carmofur, carmustine, amsacrine, doxorubicin, bruceantin, diaziquone, dideminin B, echinomycin and PCNU; anti-inflammatory steroids such as betamethasone, fludrocortisone, dexamethasone, cortisone, hydrocortisone, triamcinolone, triamcinolone acetonide, prednisone and prednisolone; estrogens such as 17β-estradiol, 17α-ethynylestradiol (ethinylestradiol), ethynylestradiol 3-methyl ether, estrone, mestranol and estriol; progestins such as dimethisterone, norethindrone, norethindrone acetate, norgestrel, norethynodrel, ethisterone, medroxyprogesterone acetate and progesterone; synthetic estrogens such as diethylstilbestrol, benzestrol, dienestrol, hexestrol and the like; immunosuppressive agents such as cyclosporine (also known as cyclosporin A); anticonvulsants such as phenytoin (diphenylhydantoin) and carbamazepine; barbiturates such as pentobarbital, phenobarbital and secobarbital, variously useful as hypnotics, anticonvulsants and sedatives; antivirals such as acyclovir, trifluridine, zidovudine, vidarabine and virazole (also known as ribavirin); vitamins/nutritional factors such as retinol (vitamin A), vitamin A-acetate, cholecalciferol, retinal, retinoic acid (also known as tretinoin or Retin-A™), isotretinoin, etretinate, acitretin and β-carotene, collectively referred to herein as retinoids, as well as other fat-soluble vitamins such as the E, D and K vitamins; β-blockers such as timolol, atenolol, propranolol, nadolol, carteolol, carvedilol, celiprolol, esmolol, labetalol, metoprolol, penbutolol, pindolol and sotalol, variously of interest not only as antihypertensives but also as anti-glaucoma agents; emetics such as apomorphine; diuretics such as chlorthalidone, furosemide and other sulfonamide-type diuretics and spironolactone, an aldosterone antagonist-type diuretic; anticoagulants such as dicumarol; cardiotonics such as digoxin and digitoxin; non-steroidal analgesics and/or anti-inflammatory agents such as aspirin, ibuprofen, indomethacin, piroxicam, sulindac and flurbiprofen; androgens such as 17-methyltestosterone and testosterone; mineral corticoids such as desoxycorticosterone; steroidal hypnotics/anesthetics such as alfaxalone; anabolic agents such as fluoxymesterone and methanstenolone; antidepressants such as sulpiride; antibiotics such as ampicillin and penicillin G; anti-infectives, such as benzalkonium chloride, cetylpyridinium chloride and chlorhexidine; coronary vasodilators such as nitroglycerin, flunarizine, lidoflazine and mioflazine; hypnotics such as etomidate; carbonic anhydrase inhibitors such as acetazolamide, chlorzolamide, ethoxzolamine, methazolamide, L-671,152 and MK-927; antifungals such as imidazole-type antifungals, e.g., econazole, clotrimazole, oxiconazole, bifonazole, metronidazole (metronidazole benzoate), fenticonazole, miconazole, sulconazole, tioconazole, isoconazole, butoconazole, ketoconazole, doconazole, parconazole, orconazole, valconazole and lombazole, and triazole-type antifungals, e.g., terconazole and itraconazole; antiprotozoals such as imidazole-type antiprotozoals, e.g., metronidazole, ornidazole, carnidazole, ipronidazole, tinidazole and nimorazole, and benzimidazole-type antifungals, e.g., flubendazole; $H_2$-antagonists, including those of the imidazole-type, e.g., burimamide, metiamide, cimetidine and oxmetidine; imidazole-type antineoplastics, such as tubulazole, a microtubule inhibitor; anthelmintic agents, including those of the benzimidazole-type, for example, thiabendazole, oxibendazole, cambendazole, fenbendazole, flubendazole, albendazole and oxfendazole; antihistaminics, including benzimidazoles such as astemizole, piperidines such as levocabastine and piperazines such as flunarizine, oxatomide and cinnarizine; antipsychotics, including those of the piperidine-type such as fluspirilene, pimozide and penfluridole; gastrointestinal agents, including piperidine derivatives such as loperamide and cisapride; serotonin antagonists, for example those of the piperidine-type such as ketanserin, ritanserin and altanserin, and those of the piperazine-type such as mianserin (also an antihistaminic); anesthetics such as lidocaine; hypoglycemics such as acetohexamide; anti-emetics such as dimenhydrinate; antibacterials such as cotrimoxazole; dopaminergic agents such as L-DOPA; anti-Alzheimer's agents such as THA; famotidine, an anti-ulcer agent/$H_2$-antagonist; benzodiazepines, for example chlordiazepoxide, diazepam, medazepam, oxazepam, lorazepam, flunitrazepam, estazolam, flurazepam, loprazolam, lormetazepam, nitrazepam, quazepam, temazepam and triazolam, variously useful as sedatives, hypnotics, anticonvulsants, tranquilizers and muscle relaxants; prostaglandins, for example PGE's such as $PGE_1$ (alprostadil), a vasodilator, and $PGI_2$ (prostacyclin or epoprostenol), a platelet inhibitor; angiotensive converting enzyme inhibitors (ACE inhibitors), such as enalaprilic acid (the diacid, sometimes called 'enalaprilate'), the ethyl ester of enalaprilic acid (sometimes called enalapril), captopril, lisinopril and SCH-33861, useful as antihypertensives; tetracycline antibiotics, such as tetracycline, chlortetracycline, oxytetracycline, demeclocycline, methacycline, doxycycline and minocycline; and macrolide antibiotics, such as erythromycin, josamycin, rosamycin, tylosin, troleandomycin and spiramycin.

In particularly preferred aspects of the present invention, the drug contemplated for use herein is a steroid, particularly an anti-inflammatory steroid (glucocorticoid) such as hydrocortisone, a steroidal estrogen such as estradiol, a synthetic estrogen such as diethylstilbestrol, a benzodiazepine such as alprazolam, or an immunosuppressive such as cyclosporin A.

In the case of aspects (C) and (D) of the invention as summarized hereinabove, the active ingredient is one of the above-described active ingredients which is insoluble or sparingly soluble in water but which also does not readily form an inclusion complex with cyclodextrin. An insoluble/ sparingly soluble active ingredient meeting this second criteria, that is, which does not readily form an inclusion complex with cyclodextrin, can be defined in terms of its solubility. Thus, an active ingredient which has a solubility of less than 10 mg/mL in 60% (weight/volume) aqueous hydroxypropyl-β-cyclodextrin at 25° C., preferably, less than 5 mg/mL, is considered an active ingredient which does not readily form an inclusion complex with cyclodextrin. Appropriate active ingredients can be readily selected from those discussed above by simply determining what their solubility is in 60% (weight/volume) hydroxypropyl-β-cyclodextrin at 25° C. Poorly soluble drugs that do not readily form cyclodextrin complexes, or do it very poorly, include: antifungal drugs such as amphotericin, clotrimazole, econazole, fluconazole, griseofulvin, intraconazole, ketoconazole, miconazole and nystatin; benzodiazepines such as alprazolam, diazepam, oxazepam and triazolam; antihypertensive agents such as allopurinol and rofecoxib; tetracyclines such as tetracycline, doxycycline and minocycline; steroids such as 17-methyltestosterone and norgestrel; retinoids such as all-trans-retinoic acid, all-trans-retinal and retinal; macrobides such as erythromycin, amphotericin B and nistatin; vitamins such as cholecalciferol; and antiviral drugs such as acyclovir.

In the case of aspects (A) and (B) of the invention as summarized hereinabove, a negatively- or positively-charged compound which forms an inclusion or non-inclusion complex with β-cyclodextrin and its inclusion complexes is required. These solubility enhancing agents, which must be acceptable for use in a pharmaceutical, cosmetic, food or agricultural composition, include negatively-charged compounds such as sodium salicylate, sodium benzoate, sodium gentisate, sodium acetate and sodium propionate; the potassium salts of such compounds; non-steroidal antiinflammatory and/or analgesic agents which are in the salt form of a carboxylic acid which has at least one benzene ring, the salt being that of an alkali-metal (e.g., sodium or potassium), alkaline-earth metal (e.g., calcium or magnesium) or aluminum. Specific salts of such aromatic ring-containing antiinflammatory or analgesic agents include amfenac sodium, bromfenac sodium, diclofenac sodium, diflumidone sodium, enolicam sodium, fenoprofen calcium, ibuprofen aluminum, indomethacin sodium, magnesium salicylate, meclofenamate sodium, naproxen sodium, sodium salicylate, tifurac sodium, tolmetin sodium and zomepirac sodium.

Thus, it can be said that suitable negatively-charged compounds fall into two groups.

The first group consists of salts of monofunctional carboxylic acids which do not form inclusion complexes with beta-cyclodextrin or do so very poorly. The term "monofunctional" refers to acids which do not have any functional groups (e.g., hydroxy groups) in addition to the carboxylic acid moiety. Such salts are typified by sodium acetate, sodium propionate and other alkali metal, alkaline-earth metal or aluminum salts of acids such as acetic and propionic.

The second group consists of salts of carboxylic acids having a lipophilic moiety or moieties that fit into the β-cyclodextrin cavity and thus form inclusion complexes with β-cyclodextrin. Often the members of this group have an aromatic moiety. Such salts are typified by sodium benzoate, sodium salicylate and the aforenoted salts of nonsteroidal antiinflammatory or analgesic carboxylic acids, all of which likewise can be alkali metal, alkaline-earth metal or aluminum salts.

Positively-charged compounds useful for this purpose include, for example, benzalkonium chloride.

In the experimental data to follow, it is shown that cyclodextrin complexes form aggregates. The consequences of the aggregate formations include the following possibilities in accord with this invention:

(a) solubilization of drugs which do not form complexes with β-cyclodextrin and its derivatives (such as 2-hydroxypropyl-β-cyclodextrin) or do it very poorly (by formation of non-inclusion complexes within the aggregates) using a compound that forms cyclodextrin complexes;

(b) solubilization of β-cyclodextrin complexes by addition of a compound that associates with the rather water-insoluble β-cyclodextrin complex aggregates (e.g., salicylate and acetate ions); and (c) stabilization and further solubilization of β-cyclodextrin complexes by addition of a small amount of a water-soluble polymer (e.g., 0.1% w/v hydroxypropyl methylcellulose) to the aggregates mentioned in (b).

Compounds which form cyclodextrin complexes which can further solubilize drugs which do not readily form cyclodextrin complexes include, for example, sodium diflunisal and cholesterol, as discussed in more detail above. Poorly soluble drugs that do not readily form cyclodextrin complexes, or do it very poorly, are likewise fully discussed above, as are the negatively-charged and positively-charged compounds that can enhance the aqueous solubility of β-cyclodextrin complexes. Also see aspects (A) through (D) of the invention summarized above.

β-Cyclodextrin and its complexes have very limited solubility in water. Thus, phase-solubility diagrams (as that shown in FIG. 8 below) frequently level off at a βCD concentration between 1 and 2% (w/v). Addition of a water-soluble polymer increases somewhat the solubility of the complex. This effect of polymers is well-documented in the literature. However, it has now been discovered that by adding sodium acetate or sodium salicylate or other charged compounds as discussed hereinabove, one can solubilize the drug/βCD complexes and observe much greater drug solubility (Examples B to E below). Addition of a polymer to such systems increases the amount of dissolved complex even further, as determined by the amount of dissolved drug. See, in particular, aspects (A) and (B) of the invention summarized above.

When a water-soluble polymer is used in a process according to the present invention, notably in aspects (B) and (D) summarized above, the aqueous medium is typically maintained from about 30° C. to about 150° C. for from about 0.1 to about 100 hours after the active ingredient is added. Other conditions useful in these processes are known, for example, from Loftsson U.S. Pat. No. 5,472,954.

In the case of aspects (C) and (D) of the invention as summarized hereinabove, in addition to the active ingredient which does not readily form an inclusion complex with cyclodextrin, a further compound is required which does form an inclusion complex with said cyclodextrin and which can be thus used to further solubilize the difficultlyγ-complexed active ingredient. This further compound, with which the complexation medium is saturated prior to adding the active ingredient, must of course be acceptable for use in a pharmaceutical, cosmetic, food or agricultural composition. In addition, it should have a log P value (where P stands for the octanol/water partition coefficient) greater than about 3.5, and preferably greater than about 4.0, in its unionized form. When ionized, the ionizable compound should preferably possess surface activity. Compounds with appropriate log P values include cholesterol (8.5), carotene (>10), dehydrocholesterol (7.8), retinoic acid (6.3), triclosan (4.8), and non-steroidal antiinflammatory drugs (NSAIDs) which have log P values of 3.5 (e.g., ibuprofen) or preferably higher, such as diclofenac (4.4), diflunisal (4.4), fenclofenac (4.8) and indomethacin (4.3). Compounds which are highly lipophilic, such as cholesterol, or which are surface active drugs, such as diflunisal, are preferred. The log P values of many compounds are known or can be readily determined by known methods.

Experiments Which Support Formation of Microaggregates:

When cyclodextrins are used to solubilize water-insoluble drugs, it is generally assumed that the solubilization proceeds through inclusion complex formation, in other words, that the lipophilic water-insoluble drug molecules, or some lipophilic moieties of the drug molecule, are taken into the hydrophobic central cavity of the water-soluble cyclodextrin molecules. Linear phase-solubility diagrams (i.e., plots showing drug solubility vs. cyclodextrin concentration) are usually assumed to indicate formation of 1:1 drug/cyclodextrin inclusion complexes or at least complexes that are first order with respect to cyclodextrin. Positive deviation from linearity is thought to indicate higher order inclusion complexes, such as formation of 1:2 drug/cyclodextrin complexes at higher cyclodextrin concentrations. Such higher order systems are characterized by stepwise binding constants, e.g., that a 1:2 complex is formed by association of the 1:1 complex with one additional cyclodextrin molecule. Frequently, the stoichiometry is obtained by simply fitting the phase-solubility diagrams to the appropriate equation without any further verification. In some cases, proposed stoichiometry and structure of a given drug/cyclodextrin complex is verified through NMR investigations. However, these are usually performed in dilute solutions, whereas the phase-solubility studies are based on investigations of saturated drug solutions. Other methods for stoichiometry verifications are based on theoretical gas-phase computer modeling of complexes that do not describe well the actual conditions in saturated aqueous solutions. Thus, the conventional descriptions of 1:1 drug/cyclodextrin complexes, as well as of those containing different stoichiometry, are not as unambiguous one might think.

Materials:

Ibuprofen and alprazolam were kindly donated by Delta (Iceland) and 17β-estradiol by Pharmatech (USA). Diflunisal was purchased from ICN Pharmaceuticals (USA), diethylstilbestrol from Norsk Medisinaldepot (Norway) and cholesterol from Sigma Chemical Co. (USA). Hydrocortisone was purchased from Norsk Medicinale Depot (Oslo, Norway). Trimethylammonium-2-hydroxypropyl-β-cyclodextrin with degree of substitution (DS) of 0.5 (TMAβCD), carboxymethyl-β-cyclodextrin sodium salt DS 0.9 (CMβCD) and randomly methylated β-cyclodextrin DS 1.8 (RMβCD) were donated by Wacker Chemie (Germany), and sulfobutylether β-cyclodextrin sodium salt DS 0.9 (SBEβCD) by CyDex (USA). 2-Hydroxypropyl-β-cyclodextrin of molar substitution 0.64 (HPβCD) was purchased from Janssen Biotech (Belgium). Polyvinylpyrrolidone of average molecular weight 40,000 (PVP) was obtained from Sigma Chemical Co. (St. Louis, Mo.), and hydroxypropyl methylcellulose 4000 (HPMC) was obtained from Mecobenzon (Copenhagen, Denmark). All other chemicals and solvents used in this study were commercially available products of analytical or special reagent grade. Semi-permeable cellophane membranes (Spectra/Por® Dialysis Tubing from regenerated cellulose) of MWCO 3,500 (No. 3), 6,000–8,000 (No. 1) and 12,000–14,000 (No. 2), as well as semi-permeable cellophane membrane (Spectra/Por® CE Dialysis membrane from cellulose esters) of MWCO 500 were purchased from Spectrum Laboratories (Houston, Tex.). The moisture content of HPβCD was periodically determined and corrected for (Scaltec SMO 01 Moisture Analyzer, Göttingen, Germany).

HPLC Analysis:

Quantitative determinations were performed in a high pressure liquid chromatographic (HPLC) system from Merck-Hitachi (Germany) consisting of L 4250 UV-Vis detector, L 6200 A Intelligent pump, AS-2000A Autosampler, D-2500 Cromato-Integrator and Phenomex Luna 5μ C18 reversed phase column (150×4.6 mm). The composition of the mobile phases and wavelengths, respectively, used for quantitative determination of the various drugs were as follows: Hydrocortisone: acetonitrile/tetrahydrofuran/water (25:1:64, v/v), 254 nm. Cholesterol: methanol, acetonitrile, isopropyl alcohol and tetrahydrofuran (50:25:25:0.1), 203 nm. Ibuprofen: acetonitrile, acetic acid and water (60:1:39), 265 nm. Diflunisal: acetonitrile, acetic acid and water (65: 2:33), 254 nm. Alprazolam: methanol and water (70:30), 254 nm. 17β-Estradiol:acetonitrile, acetic acid and water (55:1:44), 280 nm. Diethylstilbestrol:acetonitrile, ethanol and water (56:1:43), 280 nm.

Preparation of Sodium Salts:

Sodium salts of ibuprofen and diflunisal were prepared by adding 0.5 moles of each compound into 0.5 liters of aqueous 0.1 M sodium hydroxide solution. Then one liter of distilled water was gradually added to the solution and stirred overnight. The solid drug powder dissolved almost completely during this process. Finally, the filtered solution was lyophilized (Snijders Scientific 2040 lyophilizer, Holland). The lyophilized product was sieved through a 500 μm sieve.

Permeability Studies:

The permeation studies were performed in Franz diffusion cells. The donor phase consisted of a solution of hydrocortisone in aqueous HPβCD (Encapsin, Janssen Biotech) solution, which had been heated in an autoclave (121° C. for 20 min) and filtered through a 0.45 μm membrane filter. The receptor phase consisted of isotonic phosphate buffer containing 2.5% (w/v) HPβCD. A MWCO 500 or MWCO 6,000–8,000 (Spectra/Pore®, CE or No. 1 Dialysis) semi-permeable cellophane membrane was placed between the donor phase and the receptor phase and the diffusion cells maintained at ambient temperature (22–23° C.). Samples were withdrawn from the receptor phase at various time points for up to 48 hours and replaced with fresh receptor phase. The samples were analyzed for hydrocortisone by HPLC. Each experiment was repeated three times and the given values are the means ± standard deviation (T. LOFTSSON, M. MASSON AND H. H. SIGURDSSSON: Cyclodextrins and drug permeability through semi-permeable cellophane membranes. *International Journal of Pharmaceutics* 232, 35–43, 2002).

The effect of viscosity on the flux through the MWCO 6,000–8,000 membrane was determined by adding up to 0.22% (w/v) hydroxypropyl methylcellulose 4000 (HPMC) to the aqueous 5% (w/v) HPβCD solution saturated with hydrocortisone, increasing the viscosity from 1.17 to 5.45 cPoise at 22–23 ° C. (Brookfield digital viscometer).

It has been shown that the aqueous solubility of hydrocortisone increases linearly with increasing HPβCD concentration and that hydrocortisone forms a 1:1 complex with HPβCD (T. LOFTSSON, B. J. OLAFSDOTTIR AND N. BODOR: The effects of cyclodextrins on transdermal delivery of drugs. *Eur. J. Pharm. Biopharm.*, 37, 30–33, 1991). The MW of the 1:1 complex is approx. 1765 and, thus, the hydrocortisone flux from aqueous HPβCD solutions saturated with the drug through the MWCO 6,000–8,000 membrane should also increase linearly with increasing HPβCD concentrations. However, negative deviation from linearity is observed at HPβCD concentrations above about 15% (w/v) (FIG. 1). Furthermore, addition of excess HPβCD to the saturated 10% (w/v) HPβCD solution results in decreased hydrocortisone flux through the membrane (FIG. 1). The MW of the hydrocortisone/HPβCD 1:1 complex is approx. 1765. The MWCO of the membrane is about 4 times the MW of the complex.

The flux of hydrocortisone from saturated solution of the drug in water, i.e., when no HPβCD is present, through the membrane was determined to be $41\pm 6$ μg h$^{-1}$ cm$^{-2}$.

Similar results were obtained for the MWCO 12,000–14,000 membrane although hydrocortisone permeated somewhat faster through this membrane (FIG. 1). In the case of the MWCO 500 membrane, the hydrocortisone flux through the membrane was determined to be $8.9\pm 1.1$ μg h$^{-1}$ cm$^{-2}$ when no HPβCD was present in the donor phase, $14.9\pm 1.1$ μg h$^{-1}$ cm$^{-2}$ when 10% (w/v) HPβCD was present and $10.8\pm 4.8$ μg h$^{-1}$ cm$^{-2}$ when 20% (w/v) HPβCD was present. Thus, increased HPβCD concentration, and consequent increase in total amount of dissolved hydrocortisone, did not have any significant effect on the flux of hydrocortisone through the membrane. This is what should be expected since, in saturated solutions, the concentration of free hydrocortisone is constant and equal to its intrinsic solubility. Both the HPβCD molecule (molecular weight 1404) and the hydrocortisone/HPβCD complex ("molecular weight" 1765) are unable to permeate the MWCO 500 membrane.

Increasing the viscosity of the aqueous 5% (w/v) HPβCD donor solution, from 1.17 to 5.45 cPoise, did not have any effect on the hydrocortisone flux through the MWCO 6,000–8,000 membrane. The viscosity of 20% (w/v) HPβCD solution is 2.10 cPoise. The observed deviation from linearity (FIG. 1) is not due to changes in viscosity of the donor phase.

Once the MW of the aggregate exceeds the MWCO of the membranes the aggregate is unable to permeate the membrane and the flux vs. HPβCD concentration profile shows negative deviation:

Simple complexation:

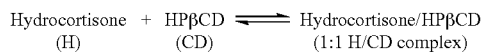

Self-association:

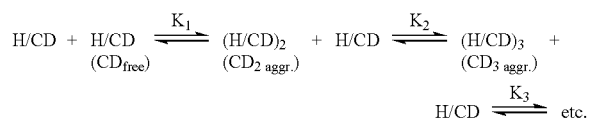

The value of K (9 M$^{-1}$) was estimated by fitting the observed flux values (FIG. 1) to the molar concentration of free hydrocortisone/HPβCD complex, and assuming that $K_1=K_2=K_3=\ldots =K$ Unusual Phase-solubility Observations:

PHASE SOLUBILITY: The phase-solubility of the sodium salts of ibuprofen and diflunisal, and that of alprazolam, 17β-estradiol and diethylstilbestrol, were determined in pH 6.0 aqueous 0.1 M phosphate buffer containing from zero to 0.1 M 2-hydroxypropyl-β-cyclodextrin (HPβCD). The phase-solubility of diflunisal sodium salt, 17β-estradiol, alprazolam and diethylstilbestrol was also determined in aqueous unbuffered solutions containing from zero to 0.1 M HPβCD. An excess of the drug was added to the aqueous solutions and the suspensions formed were heated in sealed vials in an autoclave (121° C. for 20 minutes). After equilibration at room temperature (22–23° C.) overnight, the vials were opened, small amounts of solid drug were added to each vial and the aqueous drug suspensions were allowed to equilibrate at room temperature under constant agitation for additional 6 days. The pH of the buffer solutions was monitored and kept within 0.05 pH unit from the average value. After equilibration, the suspensions were filtered through a 0.45 μm nylon membrane filter and the filtrate was analyzed by HPLC.

The effect of ionic strength on the solubilization of ibuprofen sodium salt was investigated by adding up to 12 mg/mL sodium chloride to 5% (w/v) solution of HPβCD in pH 6.0 aqueous 0.1 M phosphate buffer. These solutions were saturated with ibuprofen sodium salt as previously described.

THE EFFECT OF A SECOND DRUG: Aqueous HPβCD solutions, which previously had been saturated with the sodium salts of either ibuprofen (in pH 6.0 phosphate buffer) or diflunisal (in water), were saturated with 17β-estradiol, with diethylstilbestrol or with alprazolam through the previously described heating process in an autoclave and equilibration for 7 days at room temperature. After filtration, the concentrations of dissolved drugs were determined by HPLC.

JOB'S PLOTS: The Job's (i.e., continuous variation) plots of diflunisal and ibuprofen were determined from $^1$H-NMR (ibuprofen) or $^{19}$F-NMR (diflunisal) and UV data obtained in buffered solutions. The total molar concentration (i.e., the combined concentration of drug and HPβCD in moles per liter) was kept constant, but the mole fraction of HPβCD (i.e., [HPβCD]/([drug]+[HPβCD])) were varied from 0.1 to 0.9. The buffer salts were dissolved in 30% (v/v) D$_2$O in water and appropriate amounts of drug and HPβCD were dissolved in the buffer solution. The total concentration of diflunisal sodium salt and HPβCD was kept at 0.05 M for the $^{19}$F-NMR and $5\times 10^{-5}$ M for the UV studies. The total concentration of ibuprofen sodium salt and HPβCD was kept at 0.01 M for the H-NMR and $1\times 10^{-4}$ M for the UV studies. The NMR spectra were recorded at 297 K on a Bruker AZ250P 250 MHZ spectrometer (USA). The UV-detector used was a Perkin-Elmer Lambda 3A Spectrophotometer (USA).

MOLECULAR MODELING: Space filling docking study with Sybyl 6.6 (Tripos Inc., USA) was performed on the ibuprofen and diflunisal complexes with HPβCD.

PHASE-SOLUBILITY OF CHOLESTEROL: The phase-solubility studies of cholesterol were performed by dissolving cholesterol (20 mg/mL) in methylene chloride and evaporation of this solution (0.3 ml per vial) under a flow of nitrogen in cylindrical vials. This left a very thin layer of cholesterol on the inner surface of the vials. Aqueous cyclodextrin solutions were added to the vials and the tightly sealed vials were heated in an autoclave (121° C. for 20 minutes). After equilibration at room temperature (22–23° C.) overnight, the vials were opened, a small amount of solid cholesterol was added to each vial and the closed vials were allowed to equilibrate at room temperature for an additional 6 days.

Finally, the aqueous cholesterol suspensions were filtered through a 0.45 μm nylon membrane filter and the filtrate was analyzed by HPLC.

Figure 2:
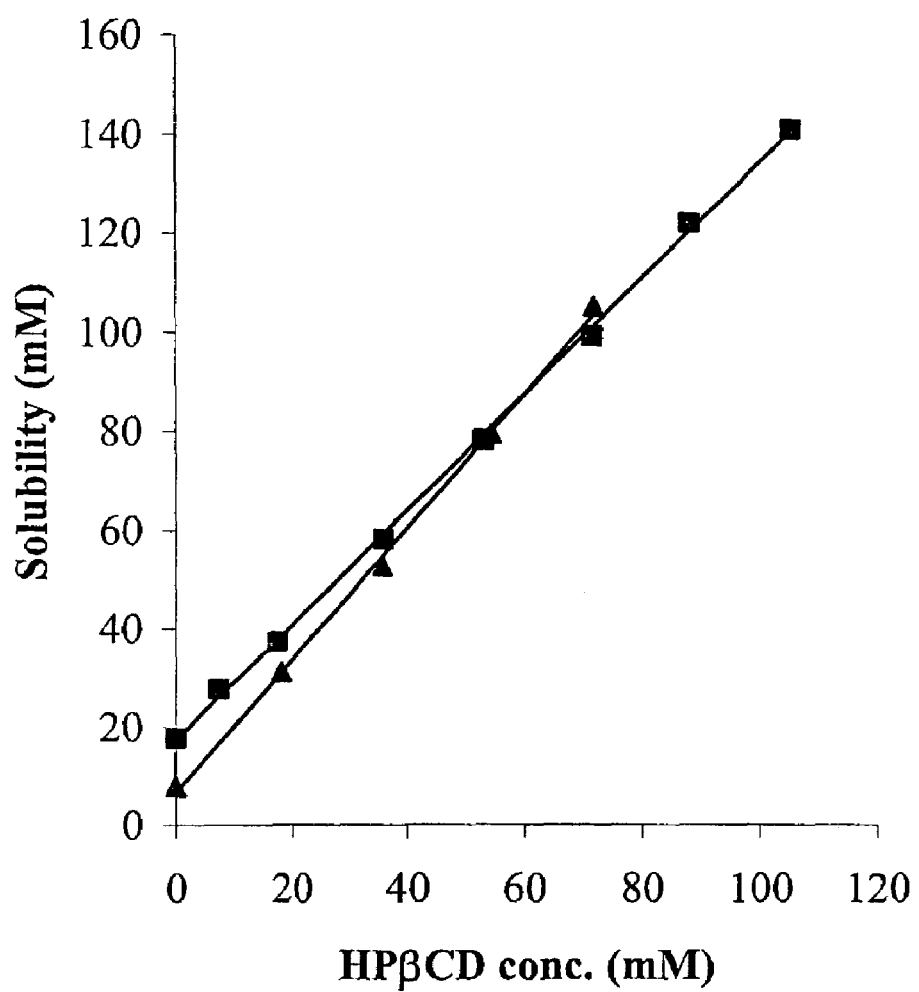
FIG. 2 is a phase-solubility diagram for the sodium salts of ibuprofen (■) and diflunisal (▲) in HPβCD containing pH 6.0 aqueous 0.1M phosphate buffer solution at ambient temperature.
Figure 3:
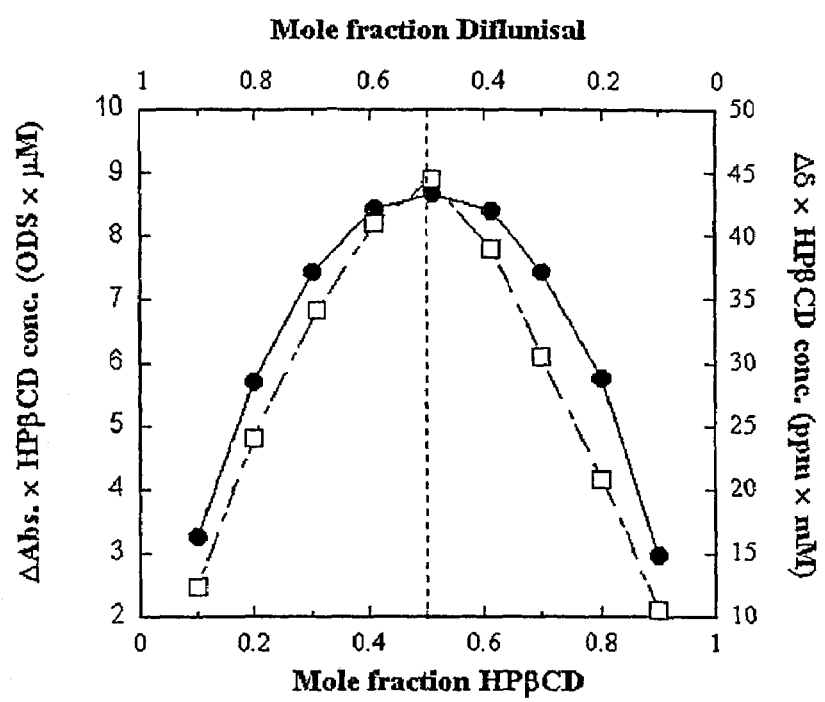
FIG. 3 is a pair of Job's plots for diflunisal sodium salt (A) and ibuprofen sodium salt (B) obtained from UV (□), $^{19}$F-NMR (graph A, ●) and $^{1}$H-NMR (graph B, ●) investigations.
Figure 3:
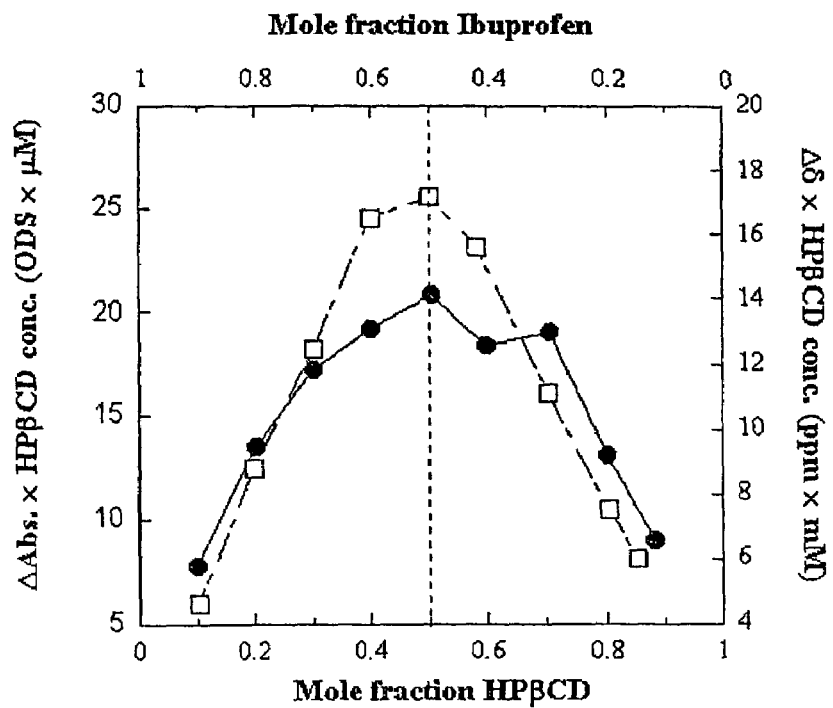

Results:

The phase-solubility diagrams of the sodium salts of ibuprofen and diflunisal in aqueous pH 6.0 HPβCD solution are shown in FIG. 2. Both diagrams are of $A_L$-type indicating that the complexes are of first order with respect to HPβCD. However, both diagrams have slopes greater than unity (i.e., 1.2 and 1.1 for ibuprofen and diflunisal, respectively) indicating that the complexes are of second or higher order with respect to the drug. The stoichiometry of the complexes was investigated by obtaining Job's plots both in NMR and UV (FIG. 3). They suggest that the mole fraction of HPβCD in both complexes is 0.5 or, in other words, that 1:1 drug/HPβCD complexes have been formed. The space filling docking study shows also that only one ibuprofen or diflunisal molecule can be fitted into the HPβCD cavity. The charged cyclodextrins and the drug salts will have significant effect on the ionic strength of the aqueous complexation media, but here an increase in ionic strength does not effect the solubility of ibuprofen in aqueous 5% (w/v) HPβCD solution. The phase-solubility diagrams could not be explained by drug supersaturation of the aqueous HPβCD solutions since addition of solid drug powder to the filtered solutions and gentle agitation for one week did not reduce the amount of dissolved drug. The solutions were stable when monitored over a period of several months. The pKa values of ibuprofen and diflunisal are 5.2 and 3.0, respectively. The pH of the aqueous buffer solution was 6.0. However, it is possible that small changes in pH could have influenced the solubility of ibuprofen sodium salt. The phase-solubility of ibuprofen sodium salt was determined at pH 6.12±0.06, 6.28±0.05 and 6.72±0.04 in aqueous 0.1 M phosphate buffer. At all three pH levels, the diagrams are of $A_L$-type with intercept ($S_0$) of 10, 20 and 40mM and slope of 1.12, 1.17 and 1.12, respectively. No correlation could be found between pH fluctuation and increase in HPβCD solubilization of the drug. Phase-solubility of the sodium salt of diflunisal in pure (i.e., unbuffered) aqueous HPβCD solutions (pH 8.36±0.09, mean value ± standard deviation) is of $A_L$-type with a slope of 1.1, or identical to the one obtained in buffered solution at pH 6.1.

The phase-solubility diagrams of alprazolam, 17β-estradiol and diethylstilbestrol in HPβCD containing pH 6.0 aqueous phosphate buffer solution are shown in FIG. 4. All three diagrams are of $A_L$-type indicating that the complexes are of first-order with respect to HPβCD. The stability of the complexes was calculated assuming 1:1 drug/HPβCD complex formation (Table 1):

TABLE 1

The inherent solubility ($S_0$), the slope of the phase-solubility diagram and the complexation efficiency (slope/(1 − slope)) of alprazolam, 17β-estradiol and diethylstilbestrol in HPβCD containing pH 6.0 aqueous phosphate buffer solutions at ambient temperature.

| Drug | $S_0$(M) | Slope | Complexation efficiency |
|---|---|---|---|
| Alprazolam | 2 $10^{-4}$ | 0.02 | 0.03 |
| Diethylstilbestrol | 1 $10^{-5}$ | 0.71 | 2 |
| 17β-Estradiol | 2 $10^{-4}$ | 0.31 | 0.4 |

For 1:1 drug/cyclodextrin complex, the complexation efficiency is defined by the following equation:

$$\text{Complexation efficiency} = S_0 \cdot K_{1:1} = \frac{[D/CD]}{[CD]} = \frac{\text{slope}}{1 - \text{slope}}$$

i.e., the concentration of the drug/cyclodextrin complex ([D/CD]) divided by concentration of free cyclodextrin ([CD]). The slope in the equation represents the slope of the phase-solubility diagram. Alprazolam has the lowest complexation efficiency of the three drugs tested or only about 0.03 (Table 1). Furthermore, the phase-solubility of alprazolam in the presence of ibuprofen (FIG. 4A) is of $A_L$-type, indicating that the complex is first order with respect to HPβCD. The concentration of dissolved ibuprofen was not affected by addition of alprazolam, diethylstilbestrol or 17β-estradiol and, since the complexation efficiency of alprazolam is very low, addition of alprazolam will have little or no effect on the ibuprofen/HPβCD complexation. If it is assumed that alprazolam is only solubilized through complexation (e.g., that the drug is not solubilized through formation of non-inclusion complexes with ibuprofen/ HPβCD complexes or ibuprofen/HPβCD aggregates), then it can be calculated that approximately 20% of HPβCD is free in the aqueous HPβCD buffer solutions saturated with ibuprofen. Based on the phase-solubility diagram for ibuprofen shown in FIG. 2 and the fraction of free HPβCD, it can be estimated that the ibuprofen:HPβCD ratio in the water-soluble complex is approximately 1.5. In other words, that for every two 1:1 ibuprofen/HPβCD complexes formed an extra ibuprofen molecule is dissolved through non-inclusion complexation.

The phase-solubility diagrams of 17β-estradiol and diethylstilbestrol (FIGS. 4B and 4C, respectively) are both non-linear, with a relatively sharp increase at HPβCD concentration of 0.02 M, resembling phase-solubility diagrams obtained in surfactant solutions.

Figure 4A:
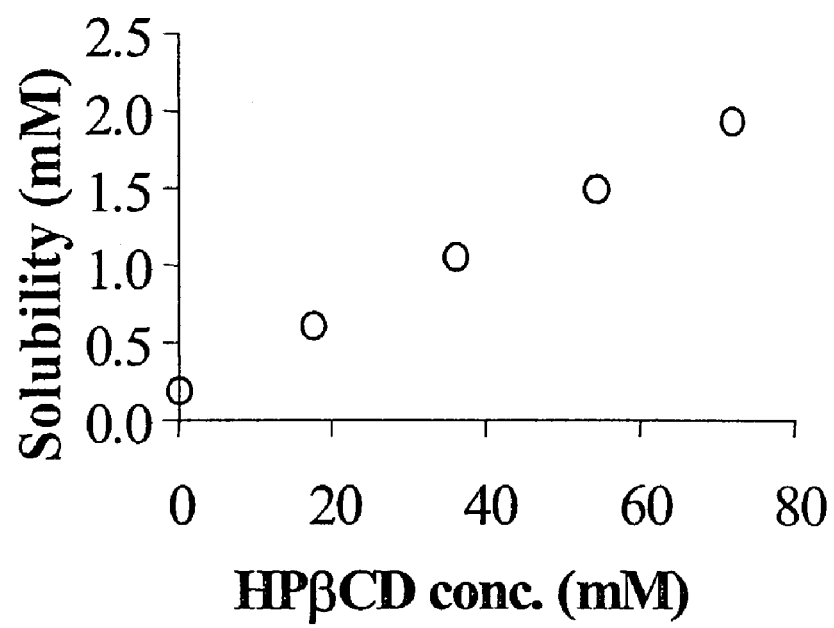
FIG. 4A is a phase solubility diagram for alprazolam in pH 6.1 aqueous 0.1 M phosphate buffer, with ibuprofen (■) and without ibuprofen (○).
Figure 4A:
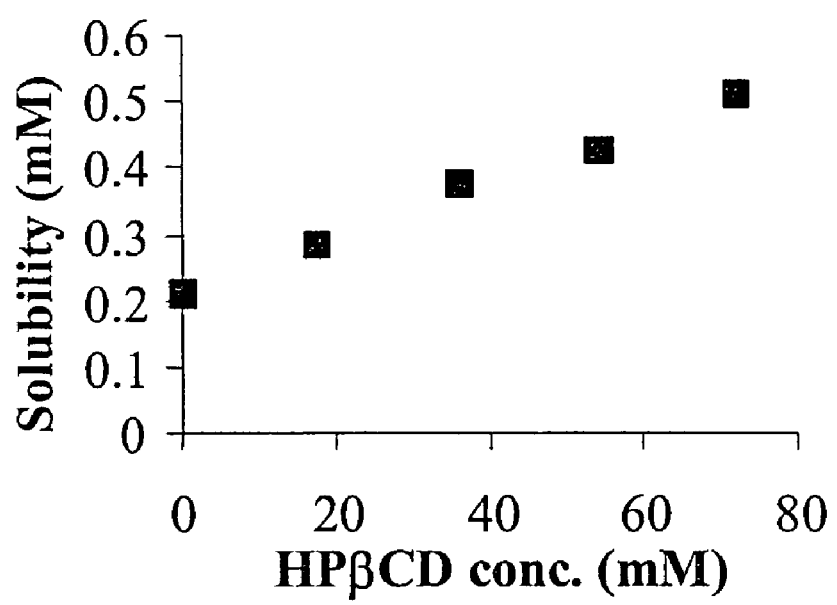
Figure 4B:
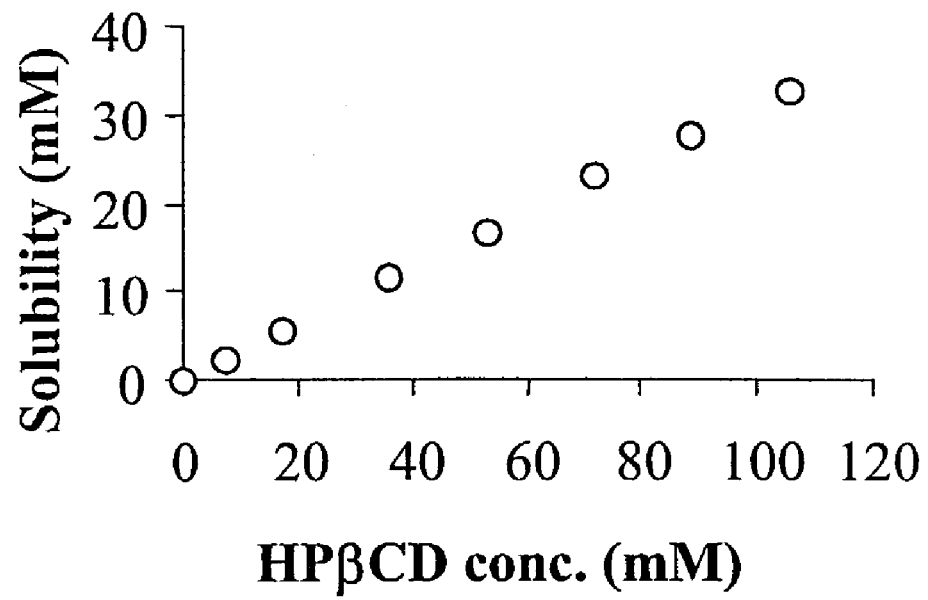
FIG. 4B is a phase solubility diagram for 17β-estradiol in pH 6.1 aqueous 0.1 M phosphate buffer, with ibuprofen (■) and without ibuprofen (○).
Figure 4B:
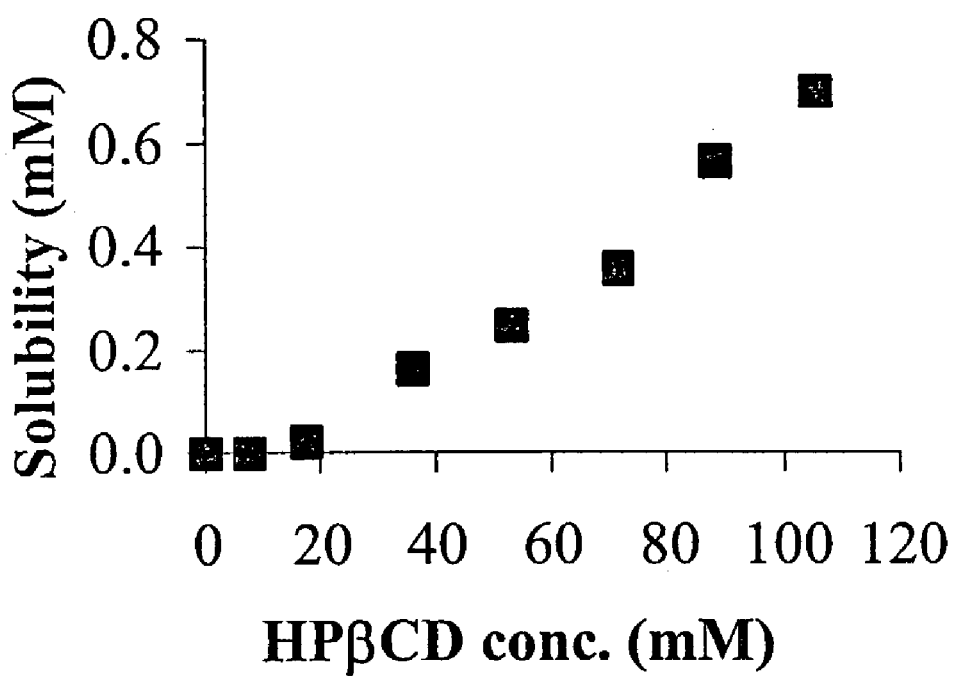
Figure 4C:
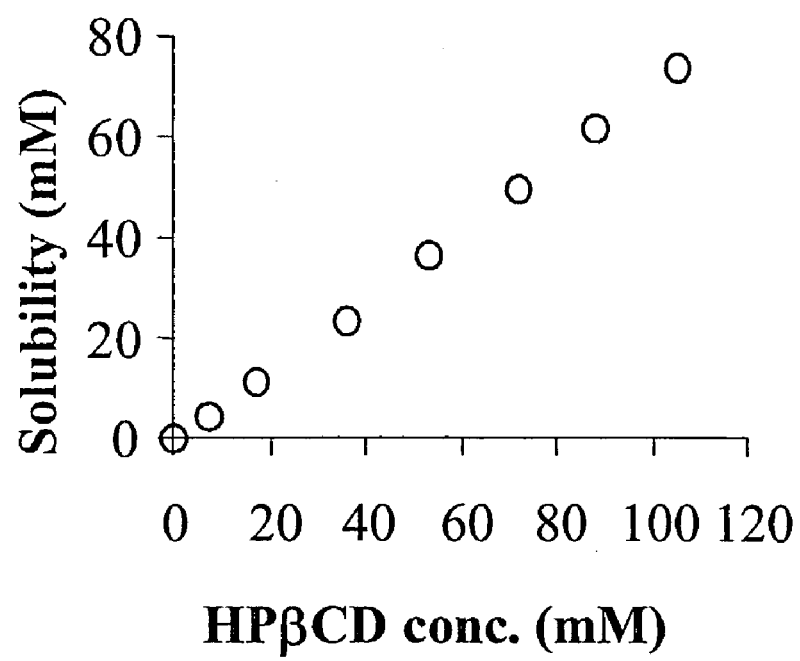
FIG. 4C is a phase solubility diagram for diethylstilbestrol in pH 6.1 aqueous 0.1 M phosphate buffer, with ibuprofen (■) and without ibuprofen (○).
Figure 4C:
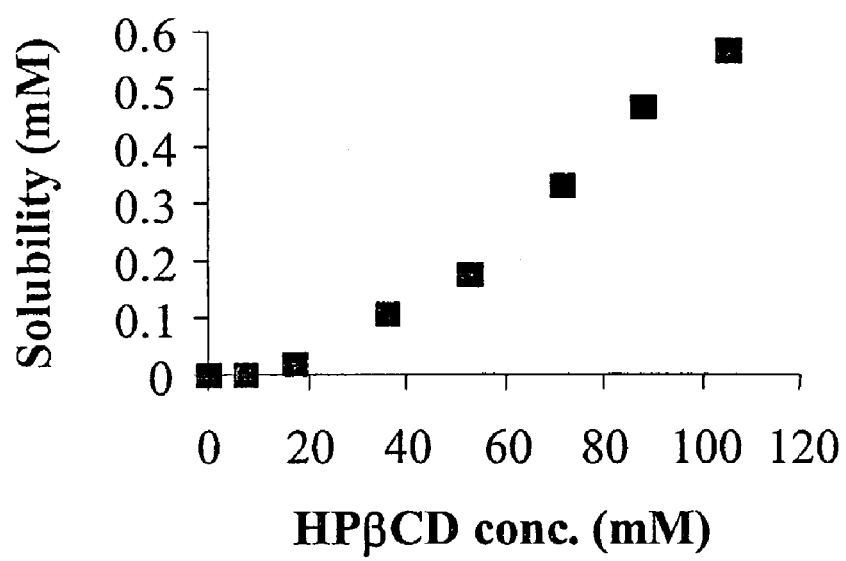
Figure 5:
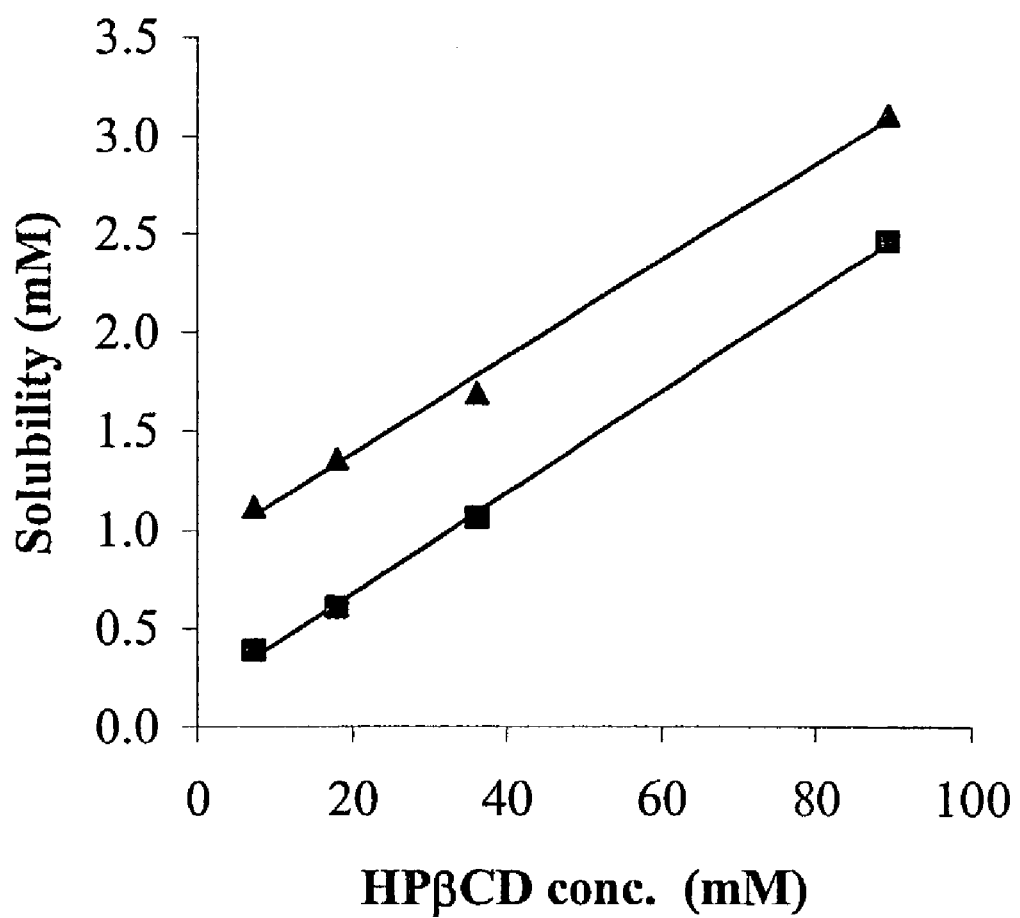
FIG. 5 is a phase solubility diagram for alprazolam in pure aqueous HPβCD solutions (■) and in aqueous HPβCD solutions which had been previously saturated with diflunisal sodium salt (▲).
Figure 6:
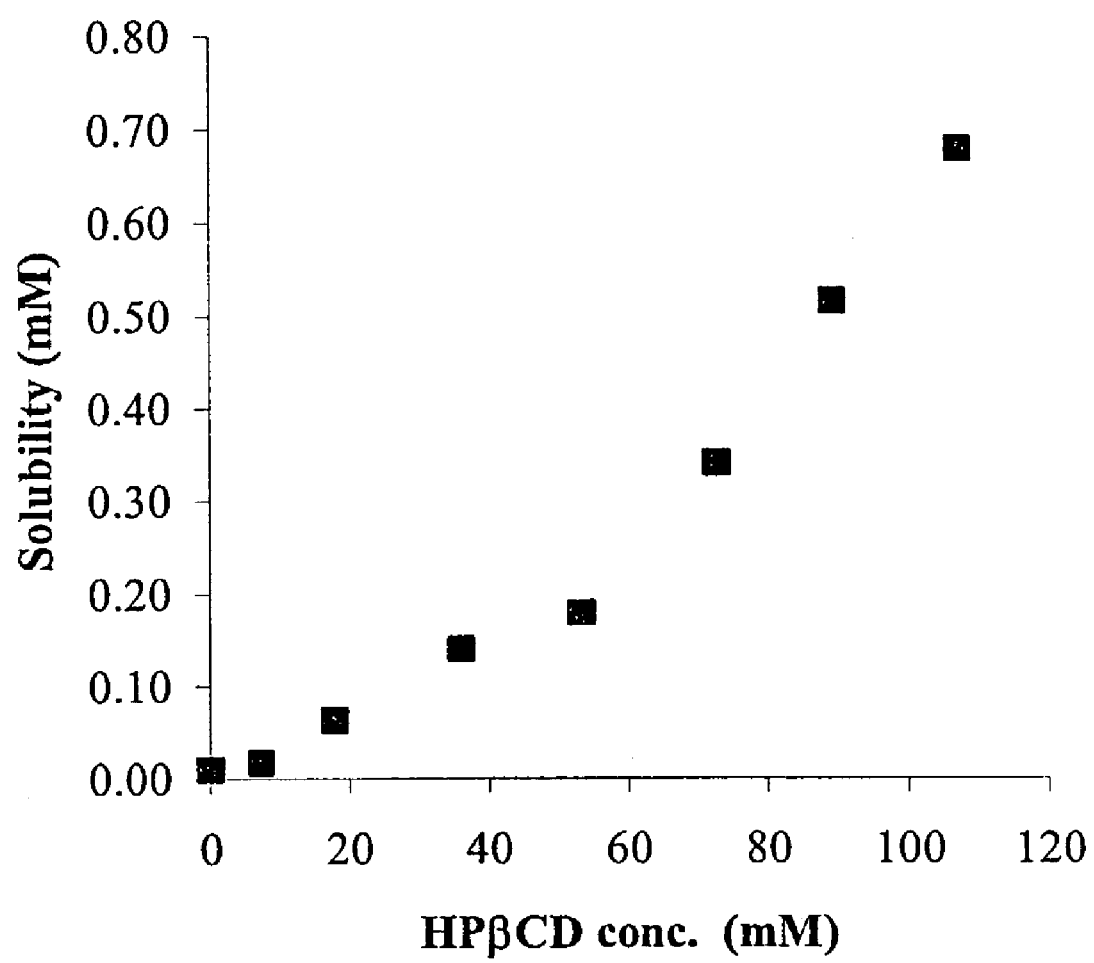
FIG. 6 is a phase solubility diagram for diethylstilbestrol in aqueous HPβCD solutions which had been previously saturated with the sodium salt of diflunisal.

The phase-solubility of alprazolam and diethylstilbestrol was determined in aqueous HPβCD solutions which had been saturated with the sodium salt of diflunisal. Addition of the drugs to the aqueous diflunisal/HPβCD solution did not lower the amount of dissolved diflunisal. As before, the phase-solubility diagram of alprazolam is linear ($A_L$-type), but in this case enhanced solubilization was observed (FIG. 5). In the case of ibuprofen, less alprazolam solubilization is observed when ibuprofen is present than when it was not present (FIG. 4A), but in the case of diflunisal the alprazolam solubilization is almost doubled. The phase-solubility diagram of diethylstilbestrol is of $A_P$-type (FIG. 6). The profile is almost identical to the one obtained in HPβCD solutions saturated with ibuprofen (FIG. 4C). Since the phase-solubility diagrams of diethylstilbestrol and 17β-estradiol are of $A_L$-type when neither ibuprofen nor diflunisal are present but of $A_P$-type when these drugs are present and less free HPβCD is available, it is highly unlikely that the positive deviation from linearity is due to formation of higher order complexes with respect to HPβCD, e.g., formation of 1:2 drug/HPβCD complex. The more likely explanation is that both diethylstilbestrol and 17β-estradiol are mainly solubilized through association with either ibuprofen/HP≠CD or diflunisal/HPβCD complexes. The same phenomenon could explain alprazolam solubilization in the presence of diflunisal (FIG. 5). Formation of guest/host complex aggregates or micelles and additional host or accompanying host solubilization within these structures can explain the observed unusual phase-solubility diagrams.

Figure 7A:
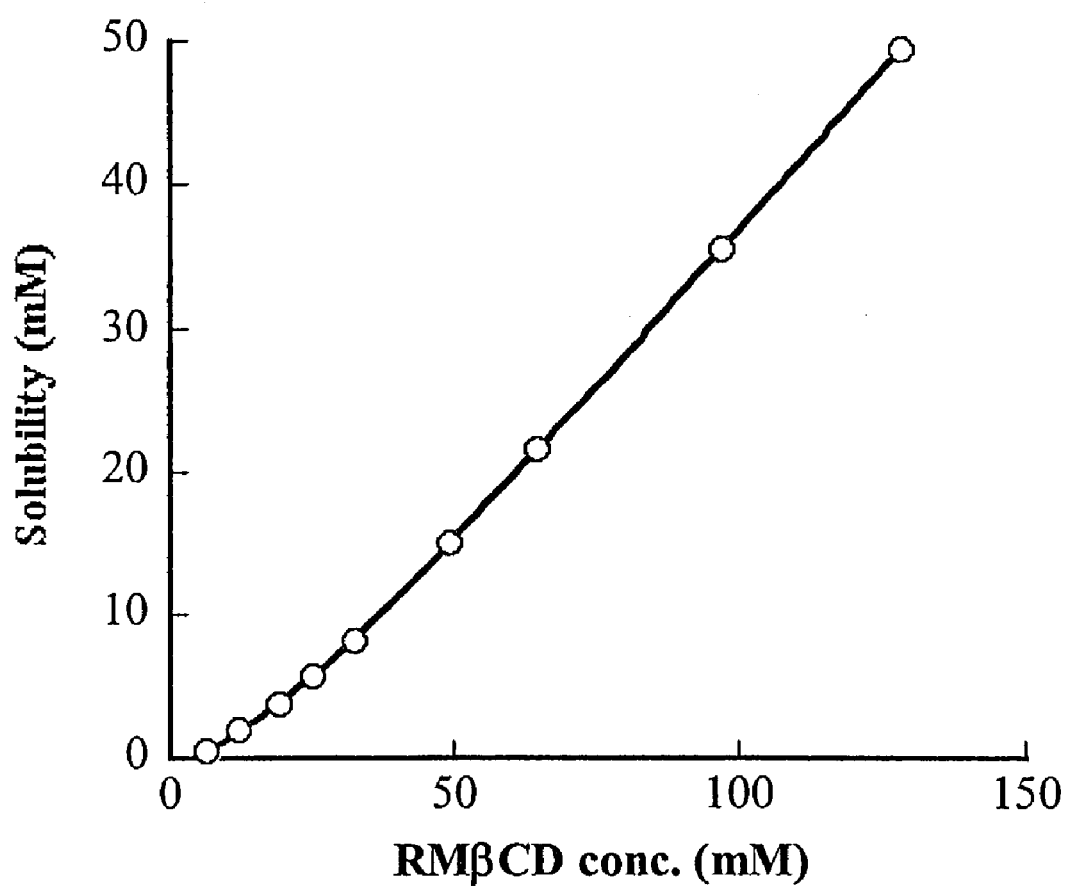
FIG. 7A is a phase solubility diagram for cholesterol in an aqueous cyclodextrin solution at ambient temperature, wherein the cyclodextrin is randomly methylated β-cyclodextrin (RMβCD) (○).
Figure 7B:
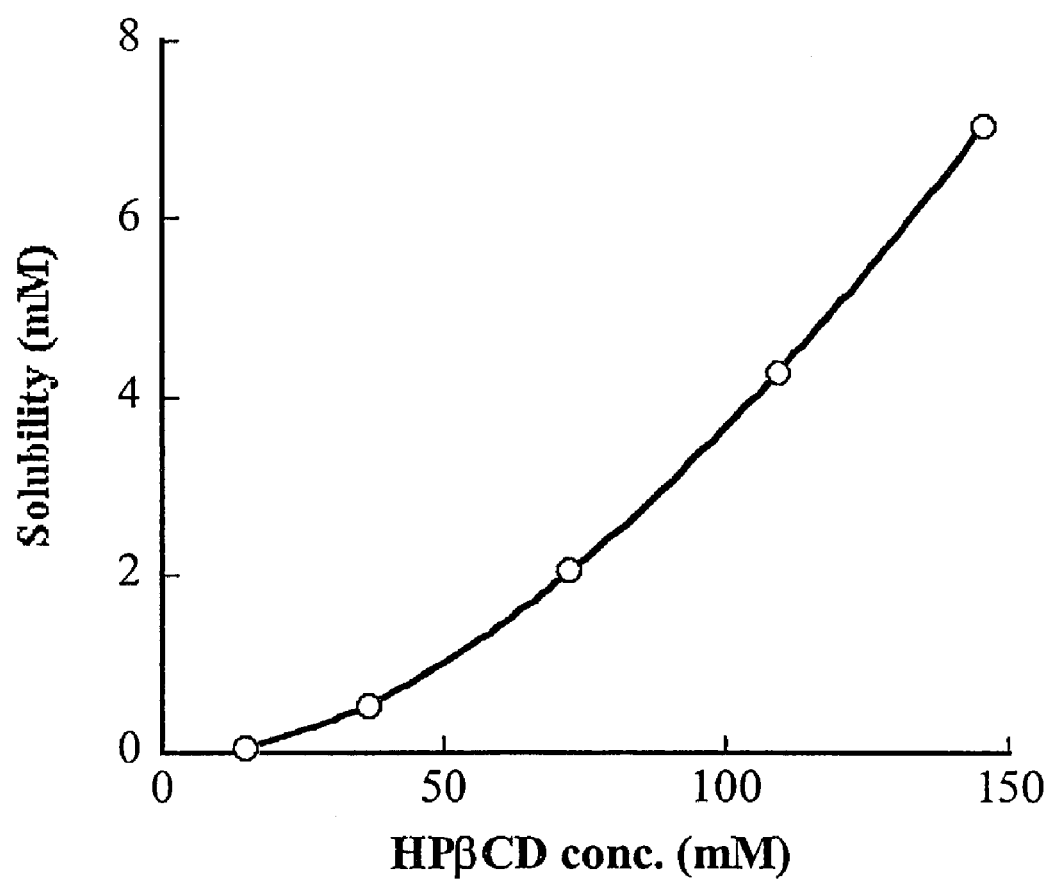
FIG. 7B is a phase solubility diagram for cholesterol in an aqueous cyclodextrin solution at ambient temperature, wherein the cyclodextrin is HPβCD (○).
Figure 7C:
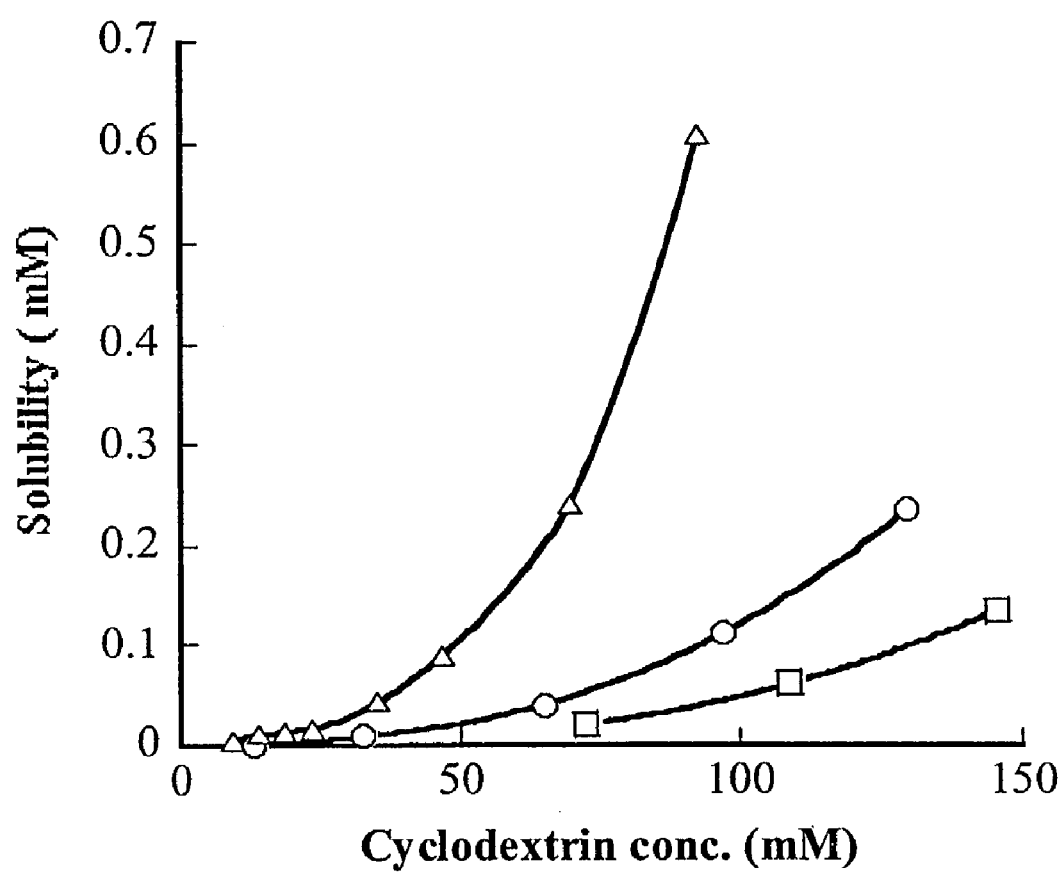
FIG. 7C is a phase solubility diagram for cholesterol in various aqueous cyclodextrin solutions at ambient temperature, wherein the cyclodextrin is sulfobutyl ether β-cyclodextrin (SBEβCD) (Δ), trimethylammonium-2-hydroxypropyl-β-cyclodextrin (TMAβCD) (○) or carboxymethyl-β-cyclodextrin sodium salt (CMβCD) (○).

FIG. 7 shows the phase-solubility diagrams of cholesterol in aqueous solutions of various β-cyclodextrin derivatives. All diagrams show positive deviation from linearity (i.e., they are of $A_P$-type), suggesting formation of second or higher order complexes with respect to cyclodextrin. Cholesterol has the highest affinity for the most lipophilic cyclodextrin, i.e., RMβCD, but lowest affinity for the very hydrophilic charged cyclodextrins. The phase-solubility diagrams for the uncharged cyclodextrins, i.e., RMβCD and HPβCD, can be fitted to a quadratic model, suggesting formation of 1:2 drug/cyclodextrin complexes. The diagrams for the charged cyclodextrins, i.e., SBEβCD, TMAβCD and CMβCD, could also be fitted to a quadratic model, but some of the functions had negative value and, thus, the equation obtained did not suggest formation of 1:2 drug/cyclodextrin complexes. It is also unlikely that two or three identical charged cyclodextrin molecules can form a complex with one small hydrophobic molecule such as cholesterol (MW 387). For example, SBEβCD (MW~2163) is an anionic β-cyclodextrin derivative with a sodium sulfonate salt separated from the hydrophobic cavity by a butyl ether spacer group. It carries, on the average, 6.5 negative charges per cyclodextrin molecule. In aqueous solutions, the repulsive electrostatic interactions between the SBEβCD molecules will most probably prevent formation of 1:2 and 1:3 drug/SBEβCD complexes. However, the shape of the phase-solubility diagrams for the ionic cyclodextrins (FIG. 7C) can be associated with surfactant type solubilization showing a relatively sharp solubilization increase at the CMC value.

Further Experiments Which Support the Present Invention:

Experiment A:

The solubility of diflunisal sodium salt and alprazolam was determined in aqueous unbuffered solution containing 10% (w/v) HPβCD. Also, aqueous HPβCD solution, which previously had been saturated with the sodium salt of diflunisal, was saturated with alprazolam. An excess of the drug was added to the aqueous solutions and the suspensions formed were heated in sealed vials in an autoclave (121° C. for 20 minutes). After equilibration at room temperature (22–23° C.) overnight, the vials were opened, a small amount of solid drug added to each vial and the aqueous drug suspensions were allowed to equilibrate at room temperature under constant agitation for additional 6 days. The pH of the unbuffered solutions was 8.36±0.09 (mean±SD). After equilibration, the suspensions were filtered through 0.45 μm nylon membrane filters and the filtrate analyzed by HPLC.

The solubility of alprazolam in 10% aqueous HPβCD solution was determined to be 0.59 mg/mL (or 1.91 mM), but 1.23 mg/mL (3.98 mM) in 10% (w/v) HPβCD solution that had previously been saturated with diflunisal. The solubility of diflunisal in 10% (w/v) HPβCD solution was unaffected by the presence of alprazolam; it was about 47 mg/mL in both cases. If no guest/host aggregates would be formed, the two drugs would compete for a space in the cyclodextrin cavity. Thus, less solubilization of alprazolam in 10% HPβCD solution would be expected when both drugs are present in a mixture compared to the alprazolam solubility when no diflunisal is present. Here, 108% increase in the alprazolam solubility is observed. The same would apply for diflunisal. If no aggregates were formed, then one would expect that the diflunisal solubility would decrease when alprazolam is added to the solution, which does not happen.

Experiment B:

The solubility of hydrocortisone was determined in aqueous unbuffered solution containing either pure water or 4% (w/v) βCD in a suspension, with and without presence of 0.25% (w/v) hydroxypropyl methylcellulose 4000 (HPMC), and sodium salicylate concentrations from 0 to 312 mM. An excess amount of hydrocortisone was added to the aqueous solutions or βCD suspension, and the hydrocortisone suspension formed was heated in a sealed vial in an autoclave (121° C. for 20 minutes). After equilibration at room temperature (22–23° C.) overnight, the vials were opened, a small amount of solid hydrocortisone was added to each vial and the aqueous suspensions were allowed to equilibrate at room temperature under constant agitation for additional 6 days. The pH of the unbuffered solutions was about 7.4. After equilibration, the suspensions were filtered through 0.45 μm nylon membrane filters and the filtrate was analyzed by HPLC.

TABLE 2

| Salicylate | Solubility of hydrocortisone (mM) | | | |
|---|---|---|---|---|
| | Pure water | | Aq. 4% (w/v) βCD susp. | |
| (mM) | No polymer | 0.25% HPMC | No polymer | 0.25% HPMC |
| 0 | 1.10 | 2.92 | 5.90 | 9.31 |
| 32 | — | — | 6.24 | 10.3 |
| 63 | 1.83 | 4.43 | 8.08 | 13.4 |
| 187 | 3.39 | 8.49 | 12.3 | 18.8 |
| 312 | 4.03 | 14.8 | 19.8 | 46.1 |

The results in Table 2 show that both salicylate and HPMC have solubilizing effect on hydrocortisone. However, in the presence of βCD, both salicylate and HPMC give a synergistic effect. For example, if additive effects would be observed, then the solubility of hydrocortisone in 4% (w/v) βCD solution containing 312 mM of salicylate should be 5.90 mM (contribution from βCD)+2.93 mM (contribution from the salicylate; 4.03–1.10 mM) or 8.83 mM. The observed value is 19.8 mM or 124% higher than the expected value. Likewise when HPMC is present one would expect hydrocortisone solubility of 9.31 mM+14.8 mM–2.92 mM or 21.2 mM. The observed value is 46.1 mM or 117% higher than the expected additive value.

Previously it has been shown that one molecule of sodium salicylate forms an inclusion complex with one molecule of βCD (formation of 1:1 inclusion complex) and that the value of the stability constant of 51 $M^{-1}$ (T. LOFTSSON AND H. FRIDRIKSDOTTIR: The effect of water-soluble polymers on the aqueous solubility and complexing abilities of β-cyclodextrin. *Int. J. Pharm.*, 163, 115–121, 1998). Thus, addition of sodium salicylate to the aqueous complexation media should result in reduced complexation and cyclodextrin solubilization of hydrocortisone. Quite unexpectedly, the addition of salicylate increases the solubilization.

hydrocortisone is 1.1 mM (0.4 mg/mL) in pure water. The maximum obtainable hydrocortisone solubility in pure aqueous βCD solutions or suspensions is 2.2 mg/mL (6.0 mM). Including 0.25% HPMC increases this value to 3.6 mg/mL (10 mM), but addition of 1% sodium acetate to the complexation medium increases the hydrocortisone solubility to 7.1 mg/mL (20 mM) (see Table 3). This is over 220% increase in the hydrocortisone solubility over the basic value of 2.2 mg/mL. The solubilization levels off at approximately 3% βCD concentration (FIG. 8 and Table 3), but at 1% when no acetate is present in the complexation media. This shows that the enhanced solubilization is partly due to increased βCD solubility and the solubility of the hydrocortisone/βCD complex. The acetate ions solubilize the hydrocortisone/βCD microaggregates formed in the aqueous solutions. Addition of HPMC to the complexation media enhances this solubilization even further (Table 3 and FIG. 8).

TABLE 3

The solubility of hydrocortisone in the aqueous complexation media when no βCD is present in the media and at the plateau (FIG. 8) where further addition of βCD does not lead to increased hydrocortisone solubility, and the approximate total βCD concentration (dissolved and undissolved) in the media where the solubilization levels off.

|  | No acetate present | | 1.0% acetate present | |
| --- | --- | --- | --- | --- |
|  | No HPMC | HPMC | No HPMC | HPMC |
| Solubility of hydrocortisone when no βCD is present | 0.4 mg/mL (1.1 mM) | 1.1 mg/mL (3.0 mM) | 1.4 mg/mL (3.8 mM) | 3.0 mg/mL (8.3 mM) |
| Approx. βCD conc. at max hydrocortisone solubility | 1% (w/v) | 1% (w/v) | 3% (w/v) | >5% (w/v) |
| Maximum hydrocortisone solubility | 2.2 mg/ml (6.0 mM) | 3.6 mg/ml (10 mM) | 7.1 mg/ml (20 mM) | >8.6 mg/ml (>24 mM) |

Figure 8:
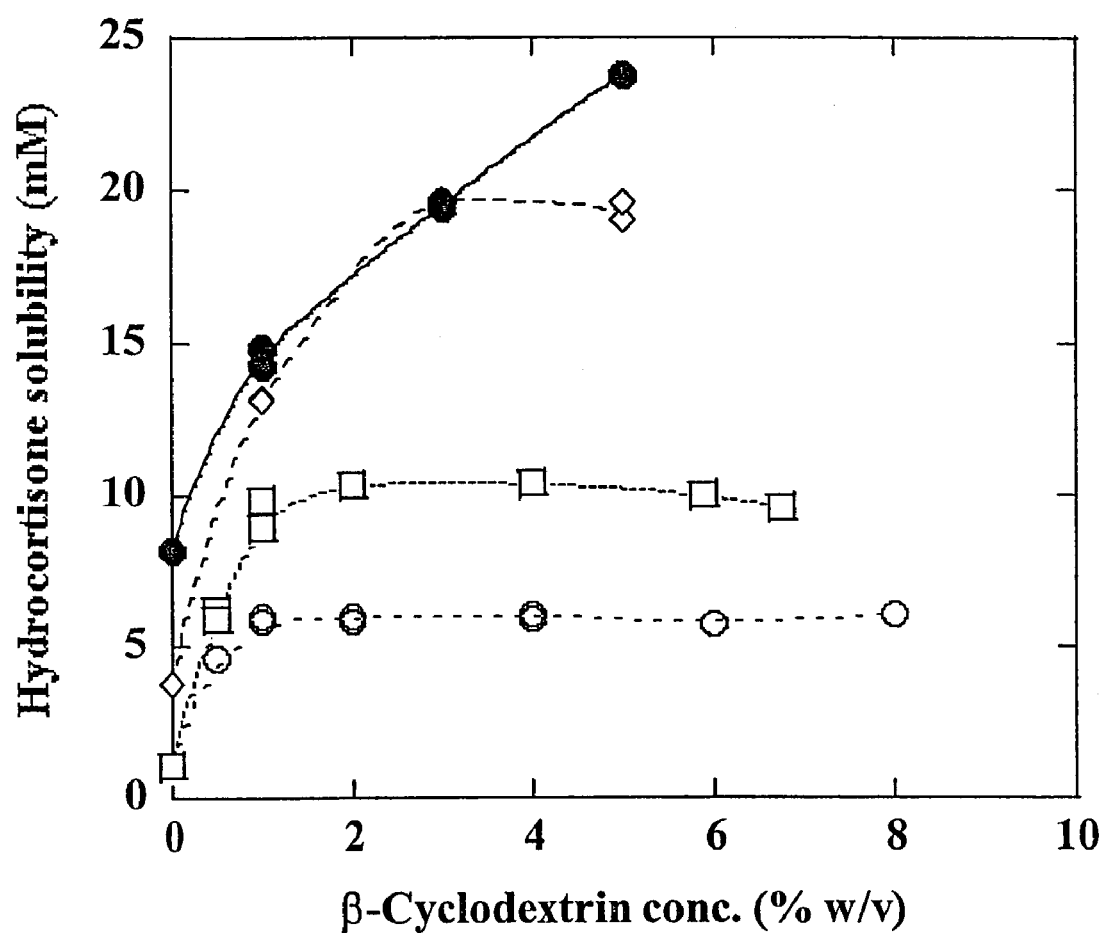
FIG. 8 is a phase solubility diagram for hydrocortisone in aqueous β-cyclodextrin (βCD) solutions or suspensions at ambient temperature, the solutions or suspensions being in pure water (○), aqueous 0.25% (w/v) hydroxypropyl methylcellulose (HPMC) solution (□), aqueous 1% (w/v) sodium acetate solution (◊), and aqueous 1% (w/v) sodium acetate solution containing 0.25% (w/v) HPMC (●).

Experiment C:

The solubility of hydrocortisone was determined in aqueous unbuffered 0 to 8% (w/v) βCD solutions or suspensions containing either no or 1% (w/v) sodium acetate, with and without the presence of 0.25% (w/v) hydroxypropyl methylcellulose 4000 (HPMC). An excess amount of hydrocortisone was added to the aqueous solutions or βCD suspension, and the hydrocortisone suspension formed was heated in a sealed vial in an autoclave (121° C. for 20 minutes). After equilibration at room temperature (22–23° C.) overnight, the vials were opened, a small amount of solid hydrocortisone was added to each vial and the aqueous suspensions were allowed to equilibrate at room temperature under constant agitation for an additional 6 days. The pH of the unbuffered solutions was about 6.9. After equilibration, the suspensions were filtered through 0.45 μm nylon membrane filters and the filtrate was analyzed by HPLC. The results are shown in FIG. 8.

Both βCD and the hydrocortisone/βCD complex have a limited solubility in water. Addition of HPMC increases the solubility. Hydrocortisone, βCD and HPMC are all uncharged compounds that do not contain moieties capable of ionization (i.e., proton acceptors or donators) at pH ranging from 1 to 12. Thus, addition of sodium acetate does not result in ionization of these compounds. It was therefore quite unexpected to find that addition of relatively small amounts of sodium acetate resulted in dramatic increase in the βCD solubilization of drugs. The aqueous solubility of Experiment D:

The solubility of hydrocortisone was determined in aqueous unbuffered 0 or 1% (w/v) βCD solutions or suspensions containing either no or 1% (w/v) benzalkonium chloride, with and without the presence of 0.25% (w/v) hydroxypropyl methylcellulose 4000 (HPMC). An excess amount of hydrocortisone was added to the aqueous solutions or βCD suspension, and the hydrocortisone suspension formed was heated in sealed vial in an autoclave (121° C. for 20 minutes). After equilibration at room temperature (22–23° C.) overnight, the vials were opened, a small amount of solid hydrocortisone was added to each vial and the aqueous suspensions were allowed to equilibrate at room temperature under constant agitation for an additional 6 days. After equilibration, the suspensions were filtered through 0.45 μm nylon membrane filters and the filtrate was analyzed by HPLC. The results are shown in Table 4. The table shows that when no polymer is present, adding 1% (w/v) benzalkonium chloride to aqueous 1% (w/v) βCD only results in slight enhancement the solubilization (increasing from 2.2 to 2.5 mg/mL), possibly due to competing effects between benzalkonium and hydrocortisone for a space in the cyclodextrin cavity. However, when the polymer is present, much greater effect is observed (increasing from 3.6 to 6.0 mg/ml), or an almost 70% increase in the solubilization.

TABLE 4

The solubility of hydrocortisone in the aqueous complexation medium when no βCD is present in the medium and when 1% (w/v) βCD is present and no or 1% (w/v) benzalkonium chloride, with and without the presence of 0.25% (w/v) hydroxypropyl methylcellulose 4000 (HPMC).

| | No benzalkonium chloride present | | 1.0% benzalkonium chloride | |
|---|---|---|---|---|
| | No HPMC | HPMC | No HPMC | HPMC |
| Solubility of hydrocortisone when no βCD is present | 0.4 mg/ml (1.1 mM) | 1.1 mg/ml (3.0 mM) | 2.6 mg/ml (7.2 mM) | 3.1 mg/ml (8.6 mM) |
| Solubility of hydrocortisone when 1% (w/v) βCD is present | 2.2 mg/ml (6.0 mM) | 3.6 mg/ml (9.9 mM) | 2.5 mg/ml (6.8 mM) | 6.0 mg/ml (16 mM) |

Figure 9:
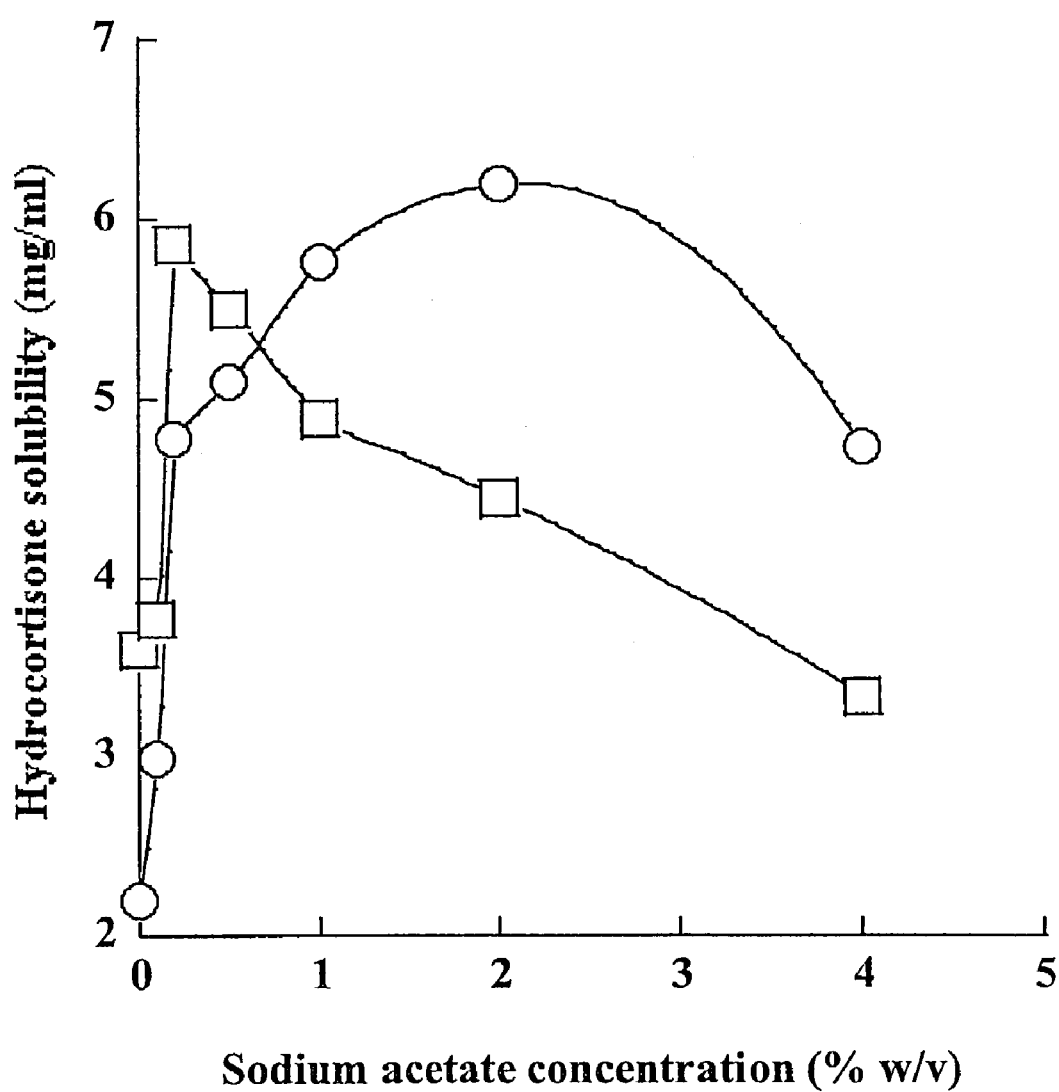
FIG. 9 is a graph showing the effect of increasing sodium acetate concentration on the concentration of hydrocortisone in aqueous 4% (w/v) βCD, in pure water (○) or in aqueous 0.25% (w/v) hydroxypropyl methylcellulose solution (HPMC) (⊔).

Experiment E:

The solubility of hydrocortisone was determined in aqueous 4% (w/v) βCD suspensions containing from 0 to 4% (w/v) sodium acetate, with and without the presence of 0.25% (w/v) hydroxypropyl methylcellulose 4000 (HPMC). An excess amount of hydrocortisone was added to the aqueous βCD suspension, and the hydrocortisone suspension formed was heated in a sealed vial in an autoclave (121° C. for 20 minutes). After equilibration at room temperature (22–23° C.) overnight, the vials were opened, a small amount of solid hydrocortisone was added to each vial and the aqueous suspensions were allowed to equilibrate at room temperature under constant agitation for an additional 6 days. After equilibration, the suspensions were filtered through 0.45 μm nylon membrane filters and the filtrate was analyzed by HPLC. The results are shown in FIG. 9. The figure shows that including a small amount of the polymer in the solutions lowers the amount of sodium acetate needed to enhance the solubilization. The hydrocortisone/βCD complex has limited aqueous solubility. Including acetate increases the solubility of the complex microaggregates. Adding polymer to the solutions stabilizes the aggregates and the involvement of acetate.

Experiment F:

The solubility of cyclosporin A was determined in aqueous unbuffered solution containing 10% (w/v) HPβCD. Also, aqueous 10% (w/v) HPβCD solution, which previously had been saturated with cholesterol, was saturated with cyclosporin A. An excess of the drug was added to the aqueous solutions and the suspensions formed were heated in sealed vials in an ultrasonic bath (70° C. for 60 minutes). After equilibration at room temperature (22–23° C.) overnight, the vials were opened, a small amount of solid cyclosporin was added to each vial and the aqueous drug suspensions were allowed to equilibrate at room temperature under constant agitation for an additional 6 days. After equilibration, the suspensions were filtered through 0.45 μm nylon membrane filters and the filtrate was analyzed by HPLC. The concentration of dissolved cyclosporin A in the solution which had not been saturated with cholesterol was determined to be 0.09 mg/mL but 0.12 mg/mL in the solution which had been saturated with cholesterol, which is a 33% increase.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A method for enhancing the aqueous solubility of an active ingredient which is insoluble or sparingly soluble in water, said active ingredient being a drug, cosmetic additive, food additive or agrochemical, said method comprising combining said active ingredient with β-cyclodextrin in an aqueous complexation medium, said medium comprising from about 0.1% to about 80% (weight/volume) of β-cyclodextrin; from about 0.1% to about 10% (weight/volume) pharmacologically inactive and pharmaceutically, cosmetically or agriculturally acceptable water-soluble polymer which is a polysaccharide, a polypeptide, a cellulose derivative, a polyoxyethylene derivative, a polyvinyl derivative or a copolymer of acrylic acid; and from about 0.1% to about 5% (weight/volume) of a negatively- or positively-charged compound which forms an inclusion or non-inclusion complex with β-cyclodextrin and its inclusion complexes, said charged compound being pharmaceutically, cosmetically or agriculturally acceptable, said negatively-charged compound being a salt of a monofunctional carboxylic acid which forms a non-inclusion complex with β-cyclodextrin or a salt of a carboxylic acid having a lipophilic moiety which forms an inclusion complex with β-cyclodextrin.

2. A method according to claim 1, wherein the pharmacologically inactive water-soluble polymer is a cellulose derivative.

3. A method according to claim 2 wherein said cellulose derivative is hydroxypropyl methyl cellulose.

4. A method according to claim 1, wherein the aqueous medium is maintained at a temperature of from about 30° C. to about 150° C. for a period of time of from about 0.1 to about 100 hours after the active ingredient is added.

5. A method according to claim 1, wherein said negatively-charged compound is a salt of a monofunctional carboxylic acid which forms a non-inclusion complex with β-cyclodextrin.

6. A method according to claim 5, wherein the salt is an alkali metal, alkaline-earth metal or aluminum salt of acetic acid or of propionic acid.

7. A method according to claim 1, wherein said negatively-charged compound is an alkali metal, alkaline-earth metal or aluminum salt of a carboxylic acid having a lipophilic moiety.

8. A method according to claim 7, wherein said salt is the salt of a nonsteroidal antiinflammatory or analgesic agent.

9. A method according to claim 8, wherein said salt is sodium salicylate, sodium benzoate or sodium gentisate.

10. A method according to claim 8, wherein said salt is amfenac sodium, bromfenac sodium, diclofenac sodium, diflumidone sodium, enolicam sodium, fenoprofen calcium, ibuprofen aluminum, indomethacin sodium, magnesium salicylate, meclofenamate sodium, naproxen sodium, sodium salicylate, tifurac sodium, tolemetin sodium or zomepirac sodium.

11. A method according to claim 1, wherein said active ingredient is a drug.

12. A method for enhancing the aqueous solubility of a drug which is insoluble or sparingly soluble in water, said method comprising combining said drug with β-cyclodextrin in an aqueous complexation medium. said medium comprising from about 0.1% to about 80% (weight/volume) of β-cyclodextrin; from about 0.1% to about 10% (weight/volume) of a pharmacologically inactive pharmaceutically acceptable water-soluble polymer which is a polysaccharide, a polypeptide, a cellulose derivative, a polyoxyethylene derivative, a polyvinyl derivative or a copolymer of acrylic acid; and from about 0.1% to about 5% (weight/volume) of a negatively-charged compound which is a salt of a monofunctional carboxylic acid which forms a non-inclusion complex with β-cyclodextrin and which is pharmaceutically acceptable.

13. A method according to claim 12, wherein the pharmacologically inactive water-soluble polymer is a cellulose derivative.

14. A method according to claim 13, wherein said cellulose derivative is hydroxypropyl methyl cellulose.

15. A method according to claim 12, wherein the aqueous medium is maintained at a temperature of from about 30° C. to about 150° C. for a period of time of from about 0.1 to about 100 hours after the drug is added.

16. A method for enhancing the aqueous solubility of a drug which is insoluble or sparingly soluble in water, said method comprising combining said drug with p-cyclodextrin in an aqueous complexation medium, said medium comprising from about 0.1% to about 80% (weight/volume) of β-cyclodextrin; from about 0.1% to about 10% (weight/volume) of a pharmacologically inactive pharmaceutically acceptable water-soluble polymer which is a polysaccharide, a polypeotide, a cellulose derivative, a oolvoxvethvlene derivative, a polyvinyl derivative or a copolymer of acrylic acid; and from about 0.1% to about 5% (weight/volume) of an alkali metal, alkaline-earth metal or aluminum salt of acetic acid or of propionic acid.

17. A method for enhancing the aqueous solubility of a drug which is insoluble or sparingly soluble in water, said method comprising combining said drug with β-cyclodextrin in an aqueous complexation medium, said medium comprising from about 0.1% to about 80% (weight/volume) of β-cyclodextrin; from about 0.1% to about 10% (weight/volume) of a pharmacologically inactive pharmaceutically acceptable water-soluble polymer which is a polysaccharide, a polypeotide, a cellulose derivative, a polyoxyethylene derivative, a polyinyl derivative or a copolymer of acrylic acid; and from about 0.1% to about 5% (weight/volume) of a negatively-charged compound which is a salt of a carboxylic acid having a lipophilic moiety which forms an inclusion complex with β-cyclodextrin and which is pharmaceutically acceptable.

18. A method according to claim 17, wherein the pharmacologically inactive water-soluble polymer is a cellulose derivative.

19. A method according to claim 18, wherein said cellulose derivative is hydroxypropyl methyl cellulose.

20. A method according to claim 17, wherein the aqueous medium is maintained at a temperature of from about 30° C. to about 150° C. for a period of time of from about 0.1 to about 100 hours after the drug is added.

21. A method according to claim 17, wherein said salt is an alkali metal, alkaline-earth metal or aluminum salt.

22. A method according to claim 21, wherein said salt is the salt of a nonsteroidal antiinflammatory or analgesic agent.

23. A method for enhancing the aqueous solubility of a drug which is insoluble or sparingly soluble in water, said method comprising combining said drug with β-cyclodextrin in an aqueous complexation medium, said medium comprising from about 0.1% to about 80% (weight/volume) of β-cyclodextrin; from about 0.1% to about 10% (weight/volume) of a pharmacologically inactive pharmaceutically acceptable water-soluble polymer which is a polysaccharide, a polypeptide, a cellulose derivative, a polyoxyethylene derivative, a polvinyl derivative or a copolymer of acrylic acid; and from about 0.1% to about 5% (weight/volume) of sodium salicylate, sodium benzoate or sodium gentisate.

24. A method for enhancing the aqueous solubility of a drug which is insoluble or sparingly soluble in water, said method comprising combining said drug with β-cyclodextrin in an aqueous complexation medium, said medium comprising from about 0.1% to about 80% (weight/volume) of β-cyclodextrin; from about 0.1% to about 10% (weight/volume) of a pharmacologically inactive pharmaceutically acceptable water-soluble polymer which is a polysaccharide, a polypeptide, a cellulose derivative, a oolvoxvethvlene derivative, a polyvinyl derivative or a copolymer of acrylic acid; and from about 0.1% to about 5% (weight/volume) of amfenac sodium, bromfenac sodium, diclofenac sodium, diflumidone sodium, enolicam sodium, fenoprofen calcium, ibuprofen aluminum, indomethacin sodium, magnesium salicylate, meclofenamate sodium, naproxen sodium, sodium salicylate, tifurac sodium, tolemetin sodium or zomepirac sodium.

* * * * *